United States Patent
Parker et al.

(10) Patent No.: US 12,128,148 B2
(45) Date of Patent: Oct. 29, 2024

(54) BIMODAL ULTRAVIOLET DISINFECTION SYSTEMS AND RELATED METHODS

(71) Applicant: LUMINII LLC, Niles, IL (US)

(72) Inventors: Jeffery Parker, Northfield, IL (US); Meng Yang, Buffalo Grove, IL (US); Laurentiu Vlad, Northfield, IL (US)

(73) Assignee: LUMINII LLC, Niles, IL (US)

( * ) Notice: Subject to any disclaimer, the term of this patent is extended or adjusted under 35 U.S.C. 154(b) by 427 days.

(21) Appl. No.: 17/488,606

(22) Filed: Sep. 29, 2021

(65) Prior Publication Data
US 2022/0096683 A1 Mar. 31, 2022

Related U.S. Application Data

(60) Provisional application No. 63/085,017, filed on Sep. 29, 2020.

(51) Int. Cl.
*A61L 2/10* (2006.01)
*A61L 9/20* (2006.01)
*G01J 1/42* (2006.01)

(52) U.S. Cl.
CPC ........ *A61L 2/10* (2013.01); *A61L 9/20* (2013.01); *G01J 1/429* (2013.01); *A61L 2202/11* (2013.01); *A61L 2202/122* (2013.01); *A61L 2202/14* (2013.01); *A61L 2202/25* (2013.01); *A61L 2209/111* (2013.01); *A61L 2209/12* (2013.01)

(58) Field of Classification Search
CPC . A61L 2/10; A61L 9/20; A61L 9/2202; A61L 9/11; A61L 9/122; A61L 9/14; A61L 9/25; A61L 2209/11; G01J 1/429
See application file for complete search history.

(56) References Cited

U.S. PATENT DOCUMENTS

| | | | |
|---|---|---|---|
| 5,961,920 A | 10/1999 | Soeremark | |
| 2005/0000365 A1* | 1/2005 | Nelsen | F24F 8/80 96/224 |
| 2009/0191100 A1* | 7/2009 | Deal | A61L 2/10 422/105 |
| 2012/0315184 A1 | 12/2012 | Clark | |
| 2013/0291735 A1* | 11/2013 | Livchak | F24F 1/0047 165/48.1 |

(Continued)

FOREIGN PATENT DOCUMENTS

WO WO-2020113149 A1 * 6/2020 .............. A61L 2/10

*Primary Examiner* — David E Smith
(74) *Attorney, Agent, or Firm* — Saul Ewing LLP

(57) ABSTRACT

A system for disinfecting an enclosed space includes a housing, ultraviolet (UV) emitters, a sensor to detect occupancy in or entry into an enclosed space, a UV directing mechanism, and a controller. The housing includes an air flow passageway. When the UV directing mechanism is in the closed state, the UV emitters are positioned in the air flow passageway and transmission of UV electromagnetic radiation into the enclosed space is substantially blocked. UV electromagnetic radiation is transmitted into the enclosed space when the UV directing mechanism is in the at least one open state. Disinfection operations can be activated when the UV directing mechanism is in the open state or the closed state. When the UV directing mechanism is in the open state, the disinfection operation is activated when the sensor indicates no occupancy in or no entry into the enclosed space.

68 Claims, 18 Drawing Sheets

(56) References Cited

U.S. PATENT DOCUMENTS

| | | | |
|---|---|---|---|
| 2016/0175475 A1* | 6/2016 | DuPuis | A61L 9/20 |
| | | | 250/504 R |
| 2016/0220716 A1* | 8/2016 | Childress | B64D 11/02 |
| 2018/0055960 A1 | 3/2018 | Reiber et al. | |
| 2021/0403176 A1* | 12/2021 | Ogram | A61L 9/20 |
| 2022/0096683 A1 | 3/2022 | Parker et al. | |

* cited by examiner

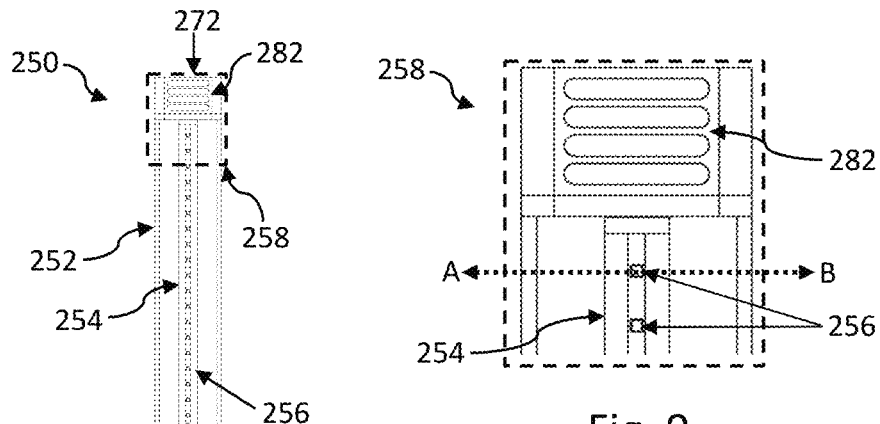
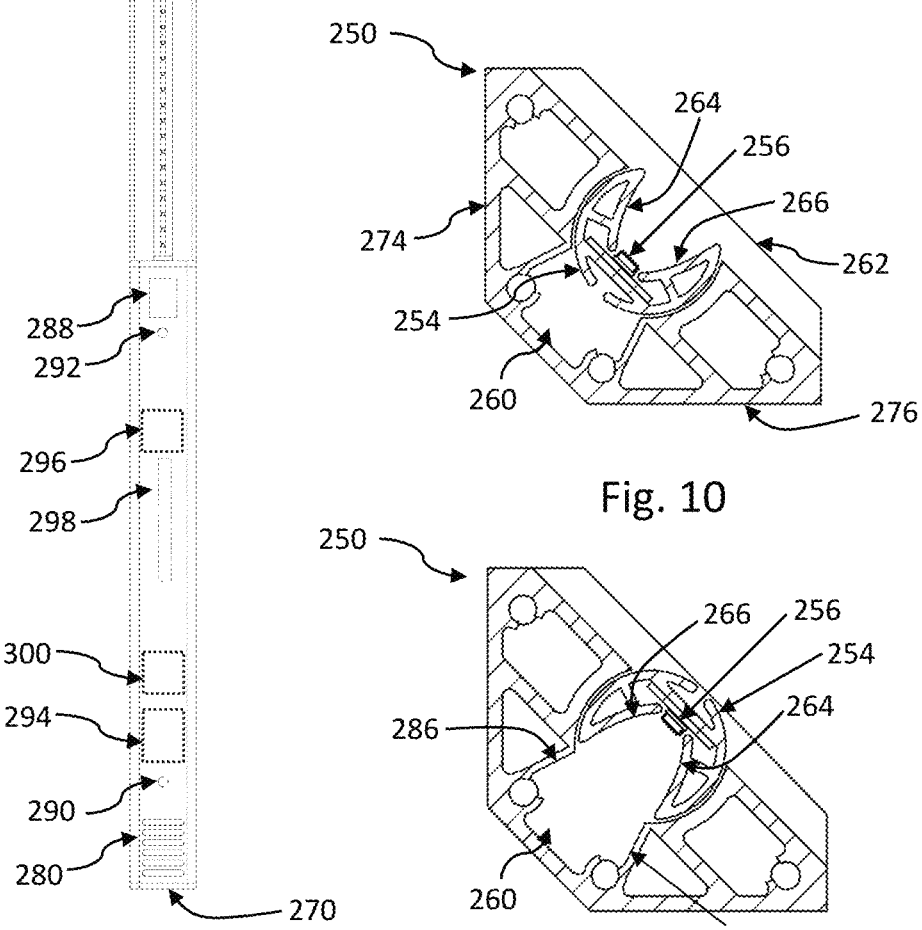
Fig. 8
Fig. 9
Fig. 10
Fig. 11

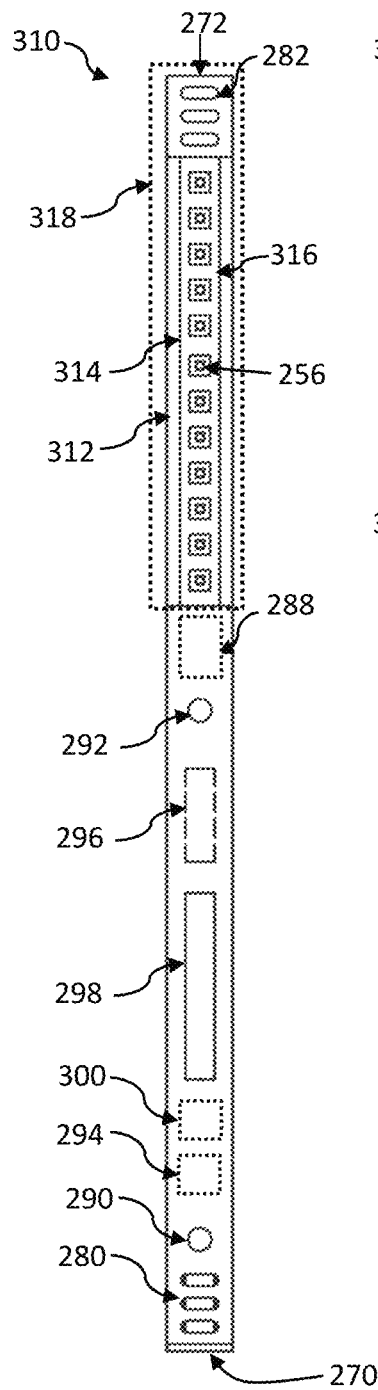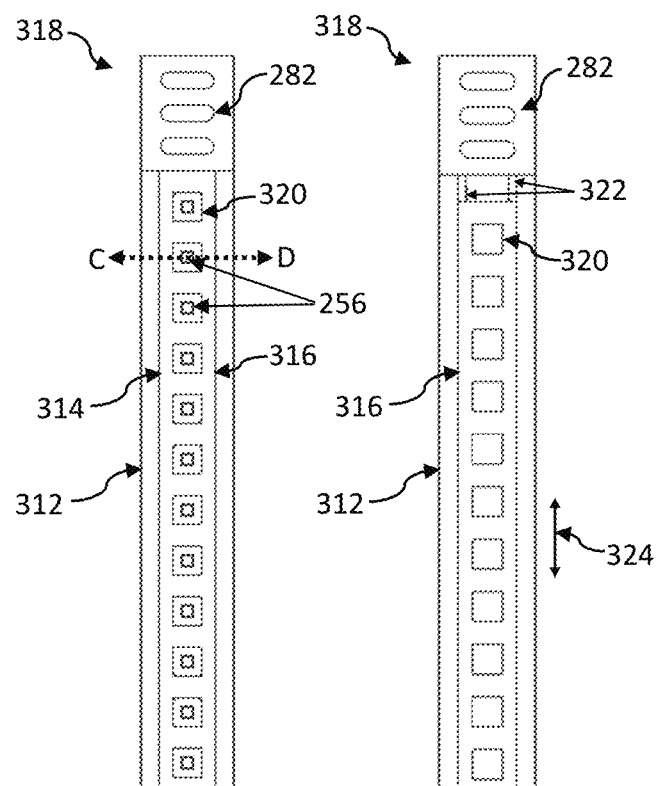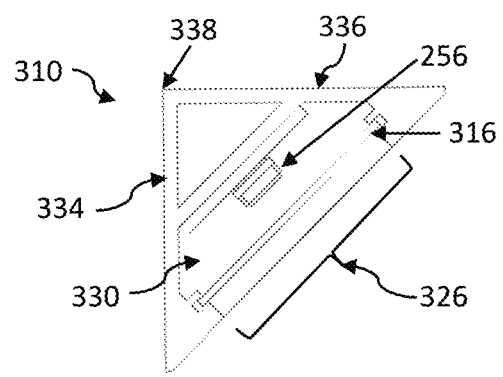
Fig. 12
Fig. 13
Fig. 14
Fig. 15

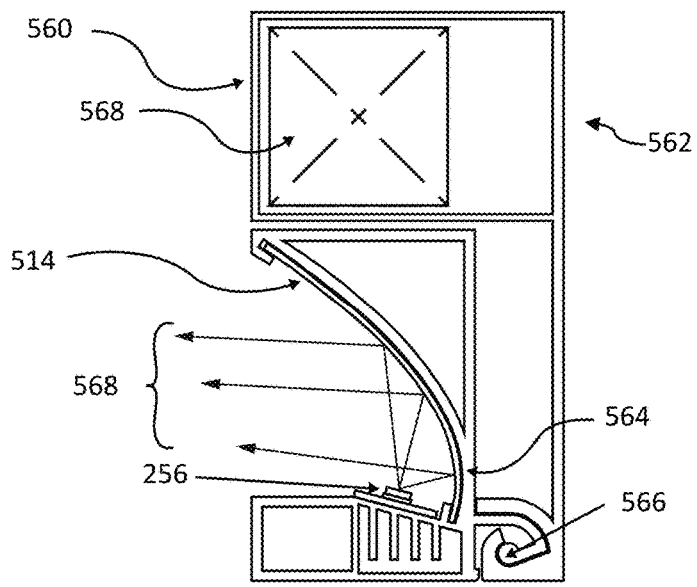
Fig. 32
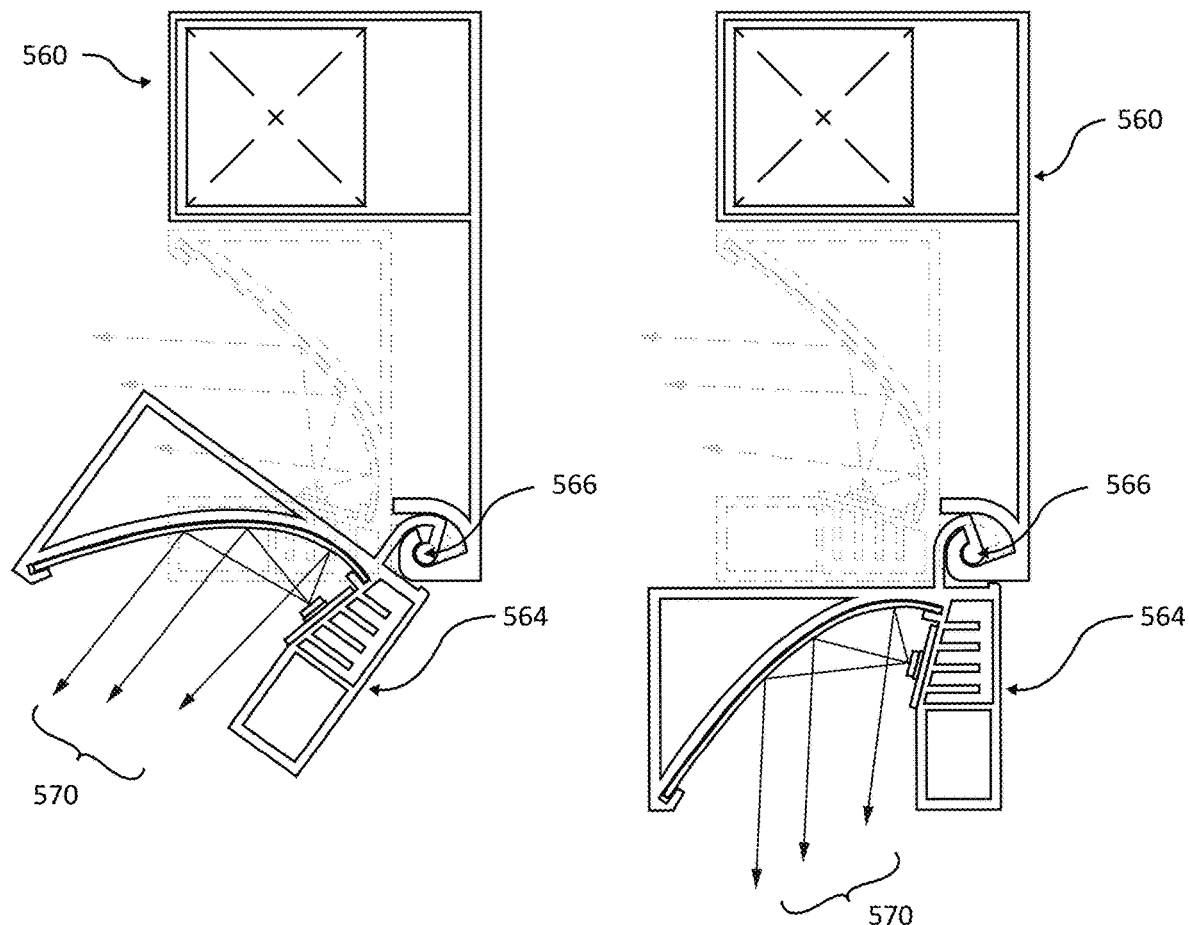
Fig. 33
Fig. 34

BIMODAL ULTRAVIOLET DISINFECTION SYSTEMS AND RELATED METHODS

CROSS-REFERENCE TO RELATED APPLICATIONS

This application claims priority from Provisional Patent Application No. 63/085,017 filed Sep. 29, 2020 and entitled "Bimodal Ultraviolet Disinfection Systems and Related Methods," the entire disclosure of which is incorporated herein by reference.

BACKGROUND

The inactivation of microorganism by ultraviolet (UV) electromagnetic radiation is a well-known phenomenon that is used in many applications. The sterilization efficiency of UV radiation depends on the wavelength range. The UV spectrum includes A-band ultraviolet (UVA) in a wavelength range of 315 nm-400 nm, B-band ultraviolet (UVB) in a wavelength range of 280 nm-315 nm, and C-band ultraviolet (UVC) in a wavelength range of 100 nm to 280 nm. A wavelength range of 200 nm to 300 nm corresponds to the peak absorption of DNA. Absorption of UV electromagnetic radiation by DNA is lethal for microorganisms. Recently, there has been increased interest in UV disinfection systems for disinfection of surfaces and ambient air. There are many different enclosed spaces where frequent and deep decontamination of surfaces and ambient air is strongly desired, such as hotel rooms, bathrooms, public buses, nursing homes, hospital rooms, airplanes, and restaurants. On the other hand, it is important to ensure that people in the enclosed space do not get exposed to UV electromagnetic radiation. Improved UV disinfection systems and methods tailored for specific disinfection operations in enclosed spaces, where people are expected to be present from time to time, are desired.

SUMMARY

In one aspect, a system for disinfecting an enclosed space includes a housing, ultraviolet (UV) emitters, a sensor to detect occupancy in or entry into the enclosed space, a UV electromagnetic radiation director, and a controller in communication with the UV emitters and the sensor. The controller controls operation of the UV emitters to carry out disinfection operations, each of a predetermined UV dose. During a disinfection operation, the UV emitters selectively emit UV electromagnetic radiation. The UV electromagnetic radiation director can be adjustable between a closed state and at least one open state. Transmission of UV electromagnetic radiation into the enclosed space can be substantially blocked when the UV electromagnetic radiation director is in the closed state. UV electromagnetic radiation can be transmitted into the enclosed space when the UV electromagnetic radiation director is in the at least one open state. The housing can also include an air flow passageway. The UV emitters can be positioned in the air flow passageway in at least one of the states of the UV electromagnetic radiation director, including the closed state. If the UV electromagnetic radiation director is in the closed state, the controller can activate the disinfection operation when first activation conditions are satisfied. If the UV electromagnetic radiation director is in the at least one open state, the controller can activate the disinfection operation when second activation conditions are satisfied. The second activation conditions can include: (2A) the sensor indicating no occupancy in or no entry into the enclosed space. The controller can suspend or deactivate the disinfection operation when the sensor indicates occupancy in or entry into the enclosed space.

In another aspect, a system for disinfecting an enclosed space can include a housing, UV emitters, a sensor to detect occupancy in or entry into the enclosed space, a UV electromagnetic radiation director, and a controller in communication with the UV emitters and the sensor. The controller controls operation of the UV emitters to carry out disinfection operations, each of a predetermined UV dose. During a disinfection operation, the UV emitters can selectively emit UV electromagnetic radiation. The UV electromagnetic radiation director can be adjustable between a closed state and at least one open state. Transmission of UV electromagnetic radiation into the enclosed space can be substantially blocked when the UV electromagnetic radiation director is in the closed state. UV electromagnetic radiation can be transmitted into the enclosed space when the UV electromagnetic radiation director is in the at least one open state. The housing can include an air flow passageway. The UV emitters can be positioned in the air flow passageway in at least one of the states of the UV electromagnetic radiation director including the closed state. The controller is in communication with the UV electromagnetic radiation director and is configured to control operation of the UV electromagnetic radiation director. If the sensor indicates no occupancy in or no entry into the enclosed space, the controller can activate or continue the disinfection operation and change the UV electromagnetic radiation director to the at least one open state when activation condition(s) are satisfied. If the sensor indicates occupancy in or entry into the enclosed space, the controller can activate or continue the disinfection operation and change the UV electromagnetic radiation director to the closed state when activation condition(s) are satisfied.

In yet another aspect, a system for disinfecting an enclosed space can include a housing, UV emitters, and a controller in communication with the UV emitters. The controller controls operation of the UV emitters to carry out disinfection operations. During a disinfection operation, the UV emitters can selectively emit UV electromagnetic radiation. At least some of the UV electromagnetic radiation can be transmitted into the enclosed space. The housing can include an air flow passageway. The UV emitters can be positioned in the air flow passageway and the UV emitters irradiate air flowing in the air flow passageway.

In yet another aspect, a system for disinfecting an enclosed space can include a housing, UV emitters for selectively emitting UV electromagnetic radiation, and a linear reflector. The housing can include an air inlet, an air outlet, and an air flow passageway. The UV emitters can be positioned in the air flow passageway and irradiate air flowing in the air flow passageway. The linear reflector can be positioned in the air flow passageway and configured to reflect the UV electromagnetic radiation towards the air outlet into the enclosed space. The linear reflector and UV emitters can be positioned such that air flowing in the air flow passageway passes between them.

The above summary of the present disclosure is not intended to describe each disclosed embodiment or every implementation of the present disclosure. The description that follows more particularly exemplifies illustrative embodiments. In several places throughout the application, guidance is provided through examples, which examples can be used in various combinations. In each instance of a list, the recited list serves only as a representative group and should not be interpreted as an exclusive list.

BRIEF DESCRIPTION OF THE FIGURES

The disclosure may be more completely understood in consideration of the following detailed description of various embodiments of the disclosure in connection with the accompanying drawings, in which:

FIGS. 8-11 are schematic views of a disinfection system including a disinfection assembly rotatable between an open state and a closed state, according to embodiments of the present disclosure.

FIGS. 12-15 are schematic views of a disinfection system including an UV shield assembly movable between an open state and a closed state, according to embodiments of the present disclosure.

FIGS. 24-29 are schematic views of disinfection systems including an UV shield assembly movable between an open state and a closed state, according to embodiments of the present disclosure.

FIGS. 32-34 are schematic cross-sectional view of a disinfection system in which a UV disinfection assembly is positionable to multiple states, according to embodiments of the present disclosure.

DETAILED DESCRIPTION OF ILLUSTRATIVE EMBODIMENTS

The present disclosure relates to enclosed space disinfection systems and related methods.

In this disclosure:

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

The terms "comprises" and variations thereof do not have a limiting meaning where these terms appear in the description and claims.

Unless otherwise specified, "a," "an," "the," and "at least one" are used interchangeably and mean one or more than one.

The recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. As appropriate, any combination of two or more steps may be conducted simultaneously.

Figure 1:
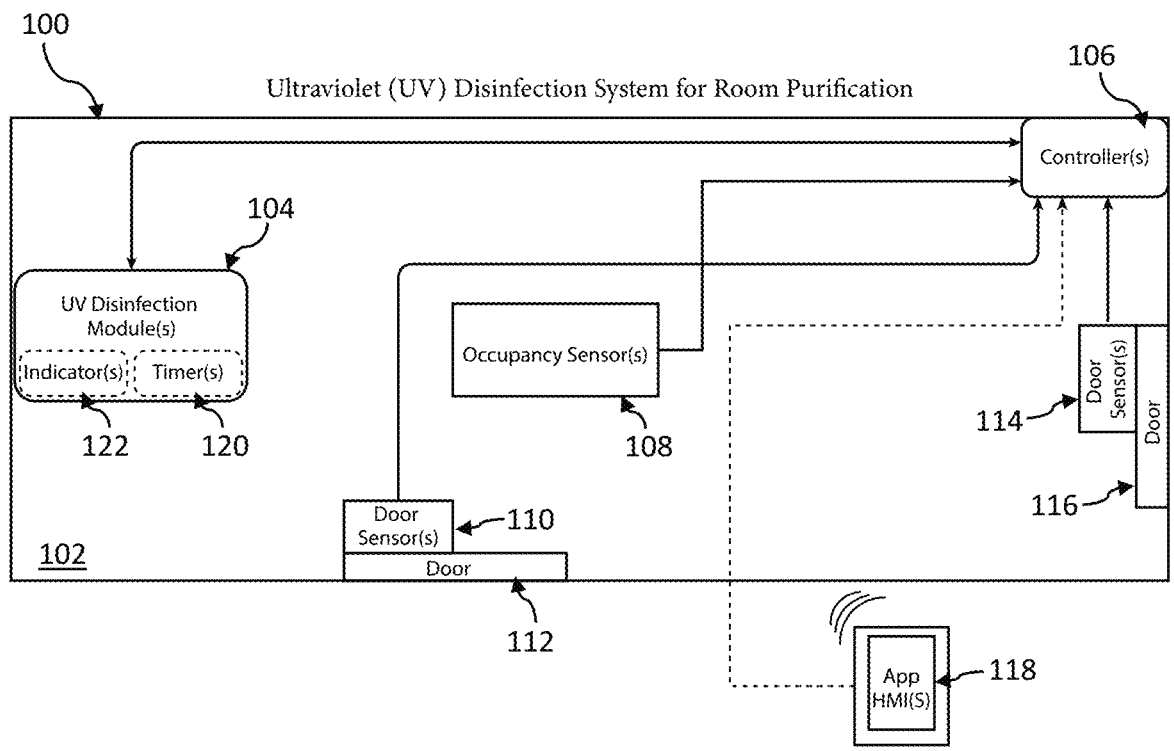
FIG. 1 is a schematic block diagram of an enclosed space disinfection system as implemented in a room of a building, according to an embodiment of the present disclosure.

FIG. 1 is a schematic block diagram of an enclosed space disinfection system 100, according to an embodiment of the present disclosure. The disinfection system 100 can be implemented in an enclosed space 102. For example, the enclosed space 102 can be a bedroom, such as a bedroom in a hotel or a nursing care facility, or any other room in a building. The disinfection system 100 includes UV disinfection assembly(ies) 104, a controller 106, occupancy sensor(s) 108, and entryway sensors 110, 114 coupled to respective entryways 112, 116 of the enclosed space 102. The UV disinfection assembly 104 can include UV emitters (not shown) for selectively emitting UV electromagnetic radiation. The UV emitters can be selected from light-emitting diodes (LEDs), laser diodes, lamps, and the like. In some cases, the UV electromagnetic radiation can be in a range of 200 nm to 300 nm. Certain details of configurations of UV emitters and UV disinfection assemblies are discussed with reference to FIGS. 8-21 and FIGS. 24-31. The UV emitters, UV disinfection assemblies, and disinfection systems discussed with reference to FIGS. 8-21 and FIGS. 24-31 can be implemented in disinfection system 100.

The occupancy sensor 108 and entryway sensors 110, 114 are examples of sensors to detect occupancy in or entry into the enclosed space 102. The occupancy sensor 108 can be a motion sensor or an acoustic sensor, for example. The entryway sensor 110, 114 can sense an opening or closing of the coupled entryway (e.g., entryway 112 for sensor 110, and the like). Since the sensor 110, 114 can be triggered by a person entering or leaving the enclosed space 102, in some cases a combination the entryway sensors and occupancy sensors can be implemented. For example, if the occupancy sensor 108 is a motion sensor and the sensor 108 detects motion immediately after an entryway sensor (e.g., sensor 110) is triggered, the controller 106 can determine that a person has entered the enclosed space 102.

The controller 106 is in electronic communication with the UV disinfection assembly 104 and the sensor(s) (108, 110, 114), and can be configured to control operation of the UV emitters of the UV disinfection assembly 104 to carry out disinfection operations. More specifically, the controller 106 can communicate with the UV emitters and can control operation of the UV emitters by communicating with and controlling a UV emitter driver circuitry. For example. if the UV emitters are LEDs, the UV emitter driver circuitry can be LED driver circuitry. The UV emitter driver circuitry is electrically connected to the UV emitters and can generate waveforms that drive the UV emitters. The UV emitter driver circuitry is electrically connected to the UV emitters and can be positioned wherever suitable, such as in the UV disinfection assembly 104, near or in the controller 106, or elsewhere in the system 100.

Figure 3:
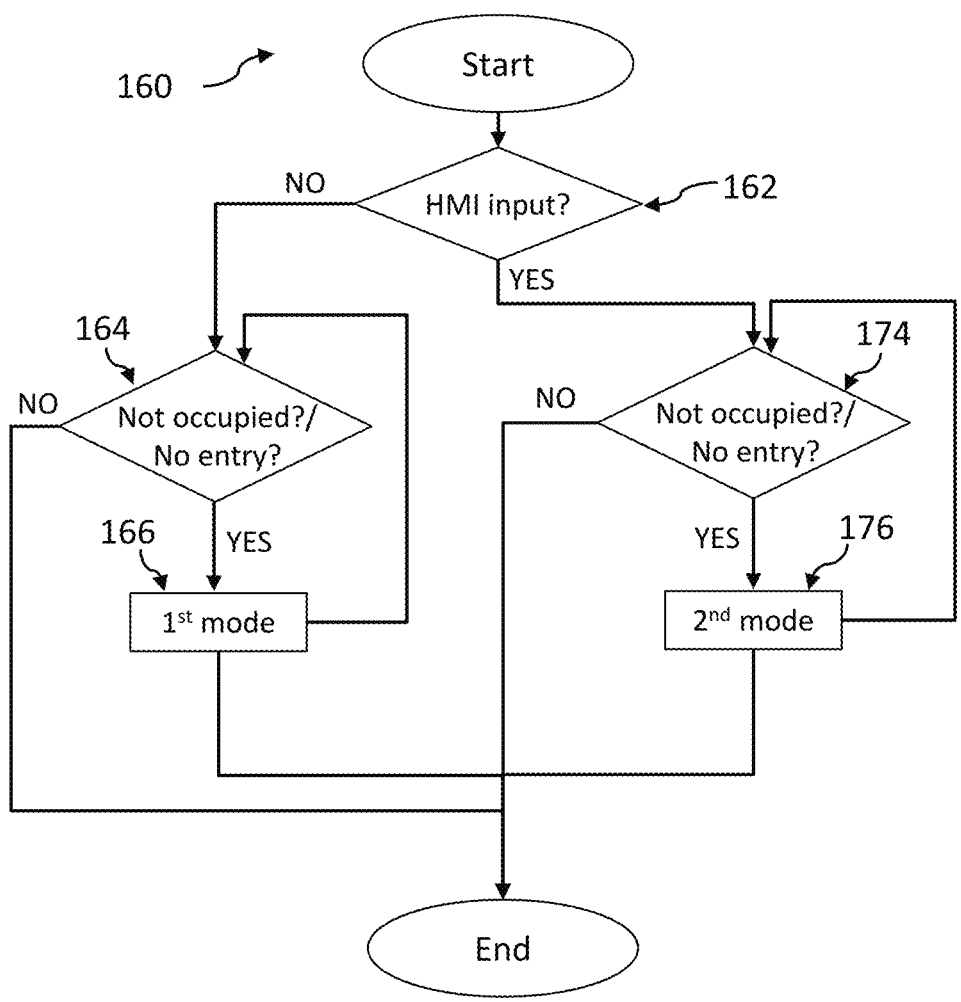
FIGS. 3-7 are flow diagrams of methods of disinfecting an enclosed space, according to embodiments of the present disclosure.

A flow diagram of a method 160 of disinfecting an enclosed space is shown in FIG. 3, according to an embodiment of the present disclosure. The method 160 can be implemented using the disinfection system 100 described in FIG. 1. The method 160 includes steps 162, 164, 166, 174, and 176. A controller, such as controller 106 of FIG. 1, can activate a disinfection operation in a first disinfection mode (first disinfection operation) when first activation conditions are satisfied. The controller can activate a disinfection operation in a second disinfection mode (second disinfection operation) when second activation conditions are satisfied. The first activation conditions can include: a determination of no qualified human input through a human-machine interface (HMI) in communication with the controller (NO branch at step 162), and a sensor (e.g., occupancy sensor 108 of FIG. 1) indicating no occupancy in or no entry into the enclosed space (YES branch at step 164). The second activation conditions can include: a qualified human input through the HMI in communication with the controller (YES branch at step 162) and the sensor indicating no occupancy in or no entry into the enclosed space (YES branch at step 174). During the disinfection operations (first disinfection mode or second disinfection mode), the controller is in communication with the sensor or sensors (e.g. occupancy sensor 108 and entryway sensors 110, 114 of FIG. 1). If the sensor(s) indicate occupancy in or entry into the enclosed space (NO branch at step 164 or 174), the controller can suspend or deactivate the respective disinfection operation. Otherwise, the respective disinfection operation can continue until the respective predetermined UV dose has been provided.

In some cases, the first disinfection operation can be carried out at any suitable time when the sensor indicates no occupancy in or no entry into the enclosed space. It may be preferable to wait a minimum inter-operation time (MIOT) since completing a previous disinfection operation, to prevent unnecessary aging of the UV emitters for example. Accordingly, the first activation conditions can additionally include: passage of a time period greater than a minimum inter-operation time (MIOT) since completion of a previous one of the disinfection operations. The second disinfection operations can be carried out if there is a qualified human input through the HMI in communication with the controller. For example, the HMI may include a software program that is executable on a mobile device (e.g., device 118 of FIG. 1), such as a mobile phone.

Referring back to FIG. 1, the system 100 can include a communication module (e.g., a wireless communication module) for communication with an external device, such as device 118. The communication module can be included in the controller 106. For example, the device 118 may be carried by housekeeping personnel who perform housekeeping activities in the enclosed space 102. The housekeeping personnel can activate the second disinfection operation before entering the enclose space in order to ensure that it is safe to enter, or after entering the enclosed space and having verified that there is no person in the enclosed space. Accordingly, in some cases the predetermined UV dose of the second disinfection operation can be greater than the predetermined UV does of the first disinfection operation (e.g., to enable a "deep clean" while the system verifies that nobody is in the enclosed space). Or in some cases the duration of the second disinfection operation can be shorter than the duration of the first disinfection operation (e.g., to enable the housekeeping personnel to enter the enclosed space more quickly). In some cases, the predetermined UV dose can be set for the first disinfection operation and/or of the second disinfection operation to be 3.0 mJ/cm2 or greater, measured at a target zone in the enclosed space 102. The target zone can be any location in the enclosed space 102 where effective disinfection of ambient air or surfaces is desired. Examples of target zones is discussed with reference to FIGS. 22 and 23.

In the disinfection system 100, the UV disinfection assembly 104 can additionally include a lifetime counter (timer) 120 and an indicator 122. The lifetime counter 120 can track the cumulative UV dose emitted by the UV emitters. The UV emitters can in some case be replaced when the cumulative UV dose reaches a predetermined cumulative UV dose (e.g., as measured by the lifetime counter 120. The indicator 122 can be a warning indicator (e.g., warning light), configured to indicate when the cumulative UV dose exceeds a predetermined cumulative UV dose for a corresponding UV emitter.

Figure 2:
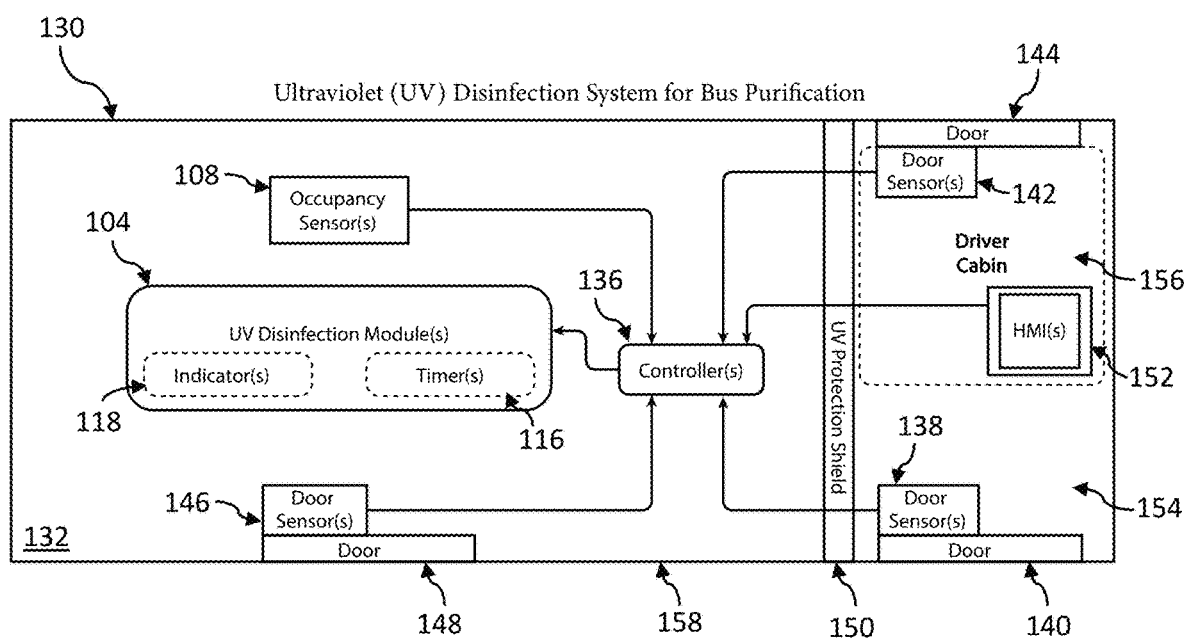
FIG. 2 is a schematic block diagram of an enclosed space disinfection system as implemented in a bus, according to an embodiment of the present disclosure.

FIG. 2 is a schematic block diagram of an enclosed space disinfection system 130, implemented in an enclosed space 132. For example, the enclosed space 132 can be an interior of a bus. The disinfection system 130 can include UV disinfection assembly(s) 104, a controller 136, a HMI 152, occupancy sensor(s) 108, and an entryway sensor 138, 142, 146 coupled to a respective entryway 140, 144, 148 of the enclosed space 132. The UV disinfection assembly 104 can include UV emitters (not shown). The UV emitters, UV disinfection assemblies, and disinfection systems discussed with reference to FIGS. 8-21 and FIGS. 24-31 can be implemented in the disinfection system 130. In the example shown, the enclosed space 132 includes a UV protection shield (UV shielding) 150. The excluded zone 154 is a zone where UV electromagnetic radiation from the UV emitters is substantially excluded by the UV shielding 150. The excluded zone 154 includes an operator cockpit 156 and the HMI 152, which is located in the operator cockpit 156. In the example shown, entryway sensors 138, 142 and their respective associated entryways 140, 144 are located in the excluded zone 154.

The controller 136 is in communication with the UV emitters of the UV disinfection assembly 104 and the sensor(s) (108, 138, 142, 146), and is configured to control operation of the UV emitters to carry out disinfection operations. The HMI 152, which receives a qualified human input, is in communication with the controller 136.

Figure 4:
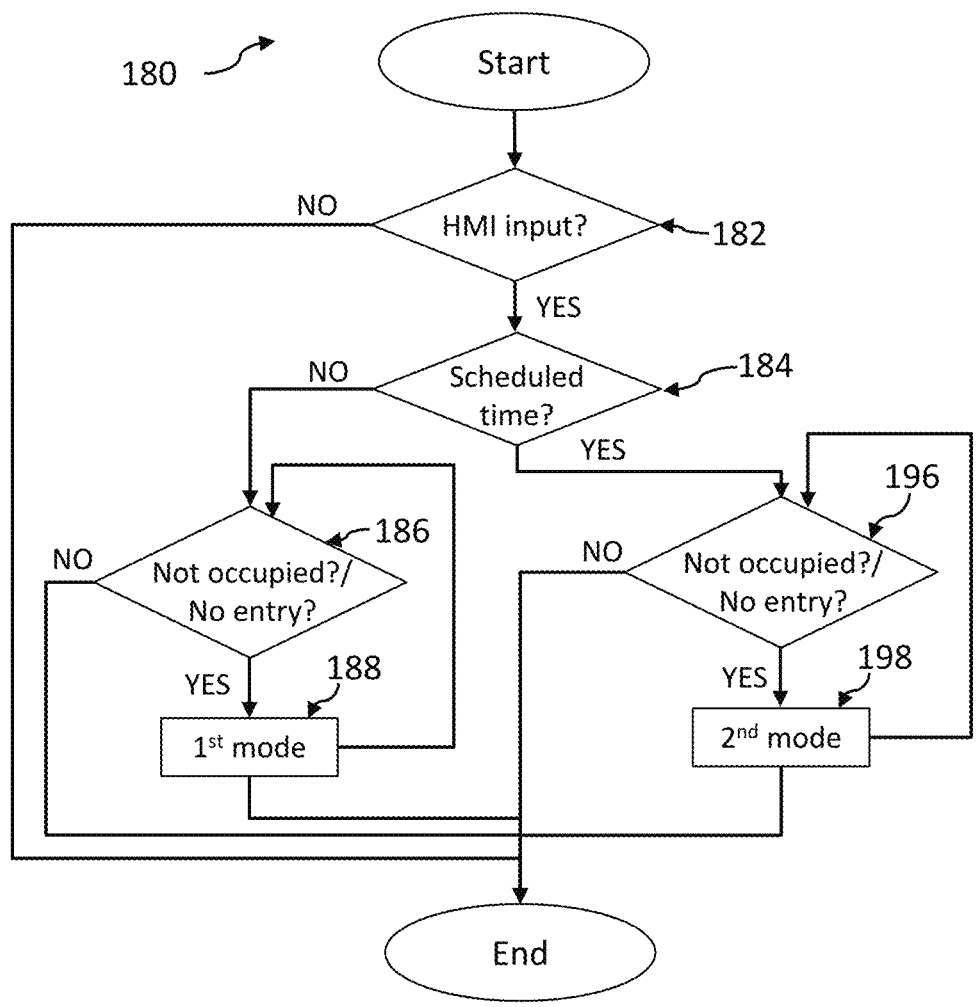

A flow diagram of a method 180 of disinfecting an enclosed space is shown in FIG. 4, according to an embodiment of the present disclosure. Method 180 can be implemented using the disinfection system 130 as described with reference to FIG. 2. The method 180 includes steps 182, 184, 186, 188, 196, and 198. A controller, such as the controller 136 of FIG. 2, can activate a disinfection operation in a first disinfection mode (first disinfection operation) when first activation conditions are satisfied. The controller can activate a disinfection operation in a second disinfection mode (second disinfection operation) when second activation conditions are satisfied. The first activation conditions can include: a qualified human input through the HMI (YES branch at step 182), the current time being outside a predetermined time period (NO branch at step 184), and the sensor indicating no occupancy in or no entry into the enclosed space (YES branch at step 186). The second activation conditions can include: a qualified human input through the HMI (YES branch at step 182), the current time being within a predetermined time period (YES branch at step 184), and the sensor indicating no occupancy in or no entry into the enclosed space (YES branch at step 196). During the disinfection operations (first disinfection mode or second disinfection mode), the controller can be in communication with the sensor(s), such as sensors 108, 110 of FIG. 2. If the sensor(s) indicate occupancy in or entry into the enclosed space (NO branch at step 186 or 196), the controller can suspend or deactivate the respective disinfection operation. Otherwise, the respective disinfection operation can continue until the respective predetermined UV dose has been reached.

In some cases, the second disinfection operations can be carried out during predetermined time periods, such as when the bus is scheduled to be parked at a bus depot for example. Accordingly, it may be preferable that the predetermined UV dose of the second disinfection operation be greater than the predetermined UV does of the first disinfection operation (to enable a "deep clean" when the bus is parked at a bus depot).

Referring back to FIG. 2, UV electromagnetic radiation from the UV emitters of the UV disinfection assembly 104 can be substantially excluded from the operator cockpit 156, as well as entryway sensors 138, 142. In some cases, the operator of the bus can remain in the operator cockpit 156 or can enter or leave the excluded zone 154 via an entryway 140 or 144 while the first disinfection operation (or the second disinfection operation) is being carried out. In some cases, the sensor(s) can be configured to detect occupancy in or entry into the enclosed space 132 except for the excluded zone 154. For example, this can be accomplished by using occupancy sensor 108 and entryway sensor 146, both of which are in the enclosed space 132 except for the excluded zone 154, and the occupancy sensor 108 can be configured to be insensitive to occupancy in the excluded zone 154. In this case, entryway sensors 138, 142 that are located in the excluded one 154 would not be used.

In some cases, the first disinfection operations can be carried out by the bus operator (providing qualified human input at the HMI) at any suitable time when the sensor indicates no occupancy in or no entry into the enclosed space (e.g., for "maintenance cleaning"). In some cases, a minimum inter-operation time (MIOT) can pass since completing a previous disinfection operation, to prevent unnecessary aging of the UV emitters for example. Accordingly, the first activation conditions can additionally include: passage of a time period greater than a minimum inter-operation time (MIOT) since completion of a previous disinfection operation.

FIG. 8 is an elevational schematic view of a disinfection system 250, including a housing 252 and a UV disinfection assembly 254 housed in the housing 252 according to an embodiment of the present disclosure. A portion 258 of the disinfection system 250 is shown in greater detail in FIG. 9. The UV disinfection assembly 254 can include an array of UV emitters 256. Two of the UV emitters 256 are shown in FIG. 9. A cross-sectional schematic view of the disinfection system 250, taken along line A-B (FIG. 9), is shown in FIG. 10. The UV disinfection assembly 254 can be rotatable along its longitudinal axis to an open state (shown in FIG. 10, as well as in FIGS. 8 and 9) and a closed state (shown in FIG. 11). In the open state, the UV emitters 256 are oriented such that UV electromagnetic radiation emitted from the emitters 256 is directed towards the front opening 262 of the disinfection system 250. In some cases, the housing 252 can be an elongate housing extending between a bottom end 270 at the floor of the enclosed space (e.g., a room) and a top end 272 at the ceiling of the enclosed space, and the housing 252 is placed in a corner of the enclosed space with its first sidewall 274 and its second sidewall 276 positioned against respective walls of the enclosed space that intersect at the corner. Accordingly, the front opening 262 can face toward the enclosed space. UV electromagnetic radiation from the UV emitters 256 can be transmitted into the enclosed space when the UV disinfection assembly 254 is in the open state. The UV disinfection assembly 254 additionally includes concave reflectors 264, 266 positioned around the UV emitters 256 to focus the UV electromagnetic radiation.

FIG. 11 shows the UV disinfection assembly 254 in a closed state, in which the UV disinfection assembly has been rotated along its longitudinal axis by approximately 180° from the orientation shown in FIG. 10. The housing 252 includes an air inlet 280 (near the bottom end 270), an air outlet 282 (near the top end 272), an air flow passageway 260 extending between the air inlet 280 and the air outlet 282. In the closed state (FIG. 11), the UV emitters 256 are positioned in the air flow passageway 260. In the closed state, the concave curved reflectors 264, 266 can be aligned with the respective sidewalls 284, 286 of the air flow passageway 260. The UV emitters 256 can irradiate the air flowing in the air flow passageway 260.

The disinfection system 250 additionally includes sensors 290, 292 to detect occupancy in or entry into the enclosed space and a controller 296 in communication with the UV emitters 256 and the sensors 290, 292. In the example shown, the controller 296 and the sensors 290, 292 are located on or in the housing 252. The sensors 290, 292 can be a motion sensor for example. The disinfection system 250 can additionally include a motor 288, configured to rotate the UV disinfection assembly 254 to the open state and the closed state. A person can select the open state or the closed state by pressing a button 292 that is coupled to the motor 288. Additionally, the controller 296 is in communication with the motor 288 and is configured to control the operation of the motor 288 to place the UV disinfection assembly 254 into the closed state or the open state. The disinfection system 250 can additionally include a power supply 294 to supply power to disinfection system components such as the motor 288, the UV emitters 256, and the controller 296. The disinfection system 250 can additionally include a warning indicator 298, visible to those in the enclosed space. The warning indicator 298 can be configured to indicate when the disinfection operation is active. The disinfection system 250 can additionally include a lifetime counter to track a cumulative UV dose emitted by the UV emitters. The warning indicator 298 can also be configured to indicate when the cumulative UV dose exceeds a predetermined cumulative UV dose. The disinfection system 250 can additionally include a fan 300 configured to move air in the air flow passageway 260 from the air inlet 280 to the air outlet 282. A fan is an example of an air mover.

Figure 5:
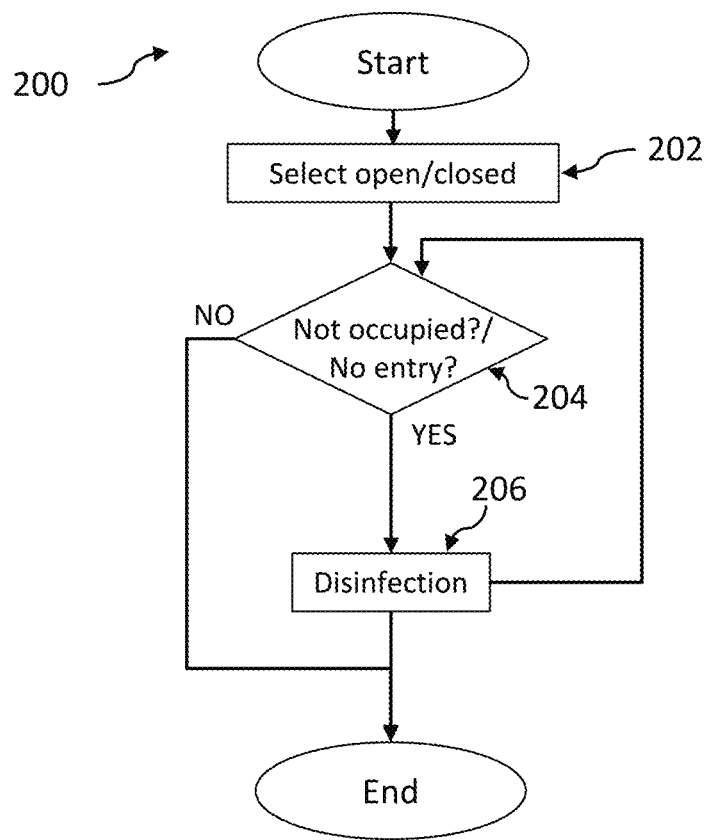

A flow diagram of a method 200 of disinfecting an enclosed space is shown in FIG. 5. In some cases, the method 200 can be implemented using the disinfection system 250 described with reference to FIGS. 8-11. The method 200 can includes steps 202, 204, and 206. At step 202, the open state (FIG. 10) or the closed state (FIG. 11) can be selected by the user (e.g., via a button). The controller (e.g., controller 296 of FIGS. 8-11) can activate a disinfection operation (step 206) when activation conditions are satisfied. The activation conditions can include: the sensor indicating no occupancy in or no entry into the enclosed space (YES branch at step 204). During the disinfection operations, the controller can be in communication with the sensor(s) (e.g., sensor(s) 290). If the sensor(s) indicate occupancy in or entry into the enclosed space (NO branch at step 204), the controller can suspend or deactivate the disinfection operation. Otherwise, the disinfection operation can continue until the respective predetermined UV dose has been reached.

Referring to FIGS. 8-11, when the rotatable UV disinfection assembly 254 is in the closed state (FIG. 11), the UV emitters 256 can be positioned in the air flow passageway 260 and the UV electromagnetic radiation from the UV emitters 256 can be transmitted into the air flow passageway 260. The air flowing in the air flow passageway can be disinfected by the UV electromagnetic radiation. The air in the air flow passageway 260 can be moved by convection and/or an air mover, such as the fan 300. Other additional advantages to this closed-state configuration can include: (1) the air flowing in the air flow passageway 260 can assist in cooling the UV emitters 256; (2) the air flowing in the air flow passageway 260 can assist in preventing the accumulation of dust and other debris from accumulating on or near the UV emitters 256; and (3) the UV emitters 256 can be protected from the external environment (e.g., the enclosed space).

According to the method 200, the controller can suspend or deactivate the disinfection operation when the sensor(s) indicate occupancy in or entry into the enclosed space. However, since transmission of UV electromagnetic radiation into the enclosed space can be substantially blocked when the UV disinfection assembly is in the closed state, the controller may refrain from suspending or deactivating the disinfection operation when the UV disinfection assembly is in the closed state.

Figure 6:
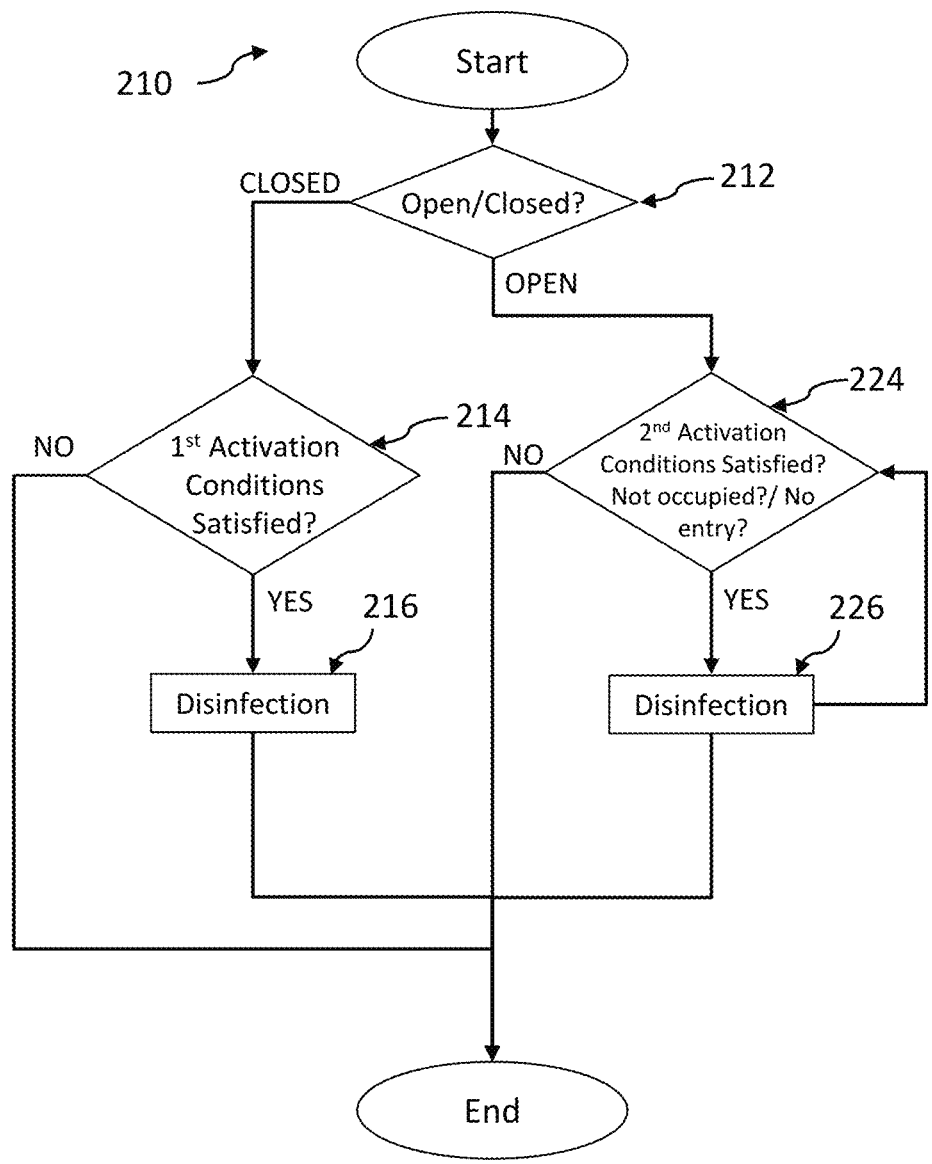

A flow diagram of a method 210 of disinfecting an enclosed space is shown in FIG. 6. The method 210 can be implemented using the disinfection system 250 as described with reference to FIGS. 8-11. The method 210 can include steps 212, 214, 224, and 226. At step 212, the open state (FIG. 10) or the closed state (FIG. 11) can be selected by user (e.g., via a button 292). If the UV disinfection assembly is in the closed state (CLOSED branch at step 212), the controller can activate a disinfection operation (step 216) when first activation conditions are satisfied (YES branch at step 214). If the UV disinfection assembly is in the open state (OPEN branch at step 212), the controller can activate a disinfection operation (step 226) when second activation conditions are satisfied (YES branch at step 224).

The first activation conditions may or may not include the sensor indicating no occupancy in or no entry into the enclosed space. The first activation conditions can in some cases include passage of a time period greater than a minimum inter-operation time (MIOT) since completion of a previous one of the disinfection operations. The second activation conditions can include: the sensor indicating no occupancy in or no entry into the enclosed space. In some cases, the second activation conditions can additionally include other conditions, such as passage of a time period greater than a minimum inter-operation time (MIOT) since completion of a previous one of the disinfection operations.

During the disinfection operations, the controller can be in communication with the sensor(s) (290). If the UV disinfection assembly is in the open state and the sensor(s) indicate occupancy in or entry into the enclosed space (NO branch at step 224), the controller can suspend or deactivate the disinfection operation (step 226). Otherwise, the disinfection operation can continue (step 226) until the respective predetermined UV dose has been reached. If the UV disinfection assembly is in the closed state, the controller can continue the disinfection operation (step 216) until the respective predetermined UV dose has been reached.

Figure 7:
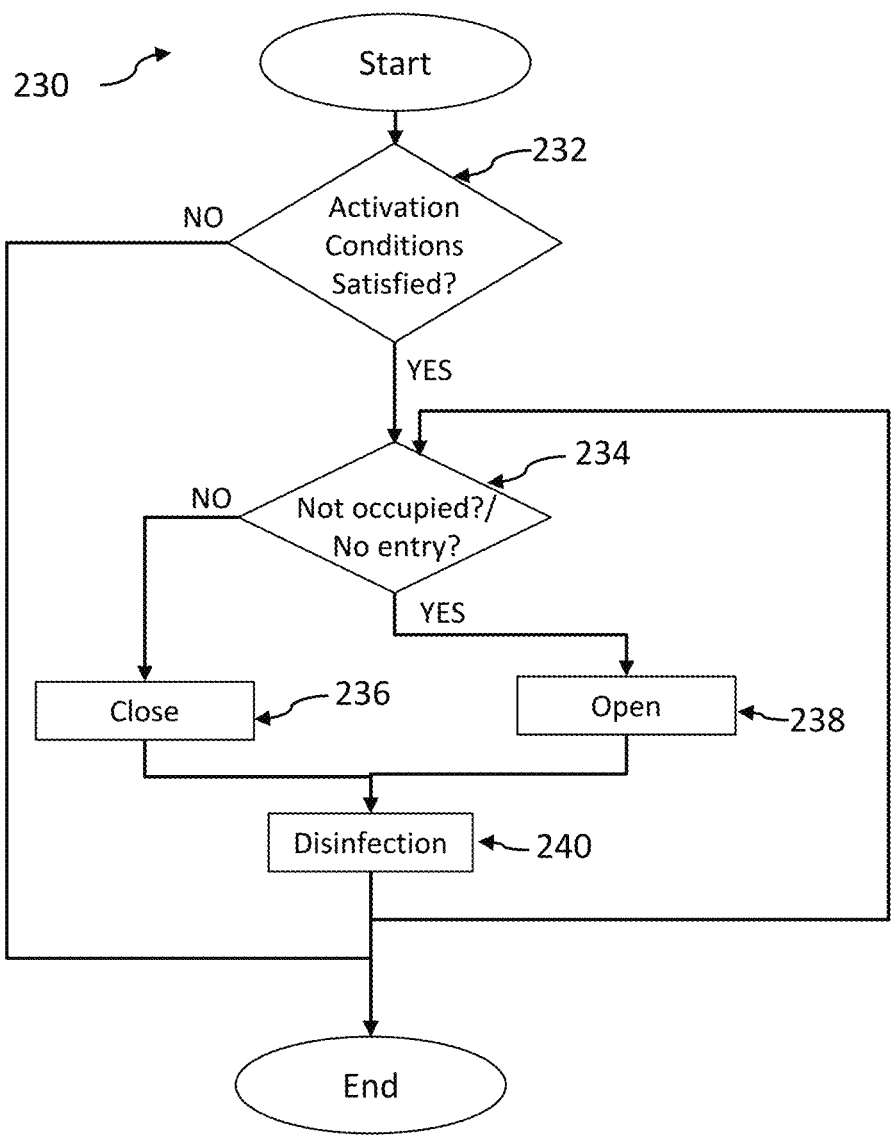

A flow diagram of a method 230 of disinfecting an enclosed space is shown in FIG. 7. The method 230 can be implemented using the disinfection system 250 described with reference to FIGS. 8-11. The method can 230 include steps 232, 234, 236, 238, and 240. A controller, such as controller 296 of FIGS. 8-11, can activate a disinfection operation (as described below) when activation conditions are satisfied (YES branch at step 232). The sensor indicating no occupancy or no entry into the enclosed space may not be an activation condition. For example, the activation conditions can include one or more of the following: (A) passage of a time period greater than a minimum inter-operation time (MIOT) since completion of a previous one of the disinfection operations; (B) a qualified human input through a HMI in communication with the controller; and (C) an indication of contamination in the enclosed space from a contamination sensor in communication with the controller. In this context, a contamination sensor need not be capable of measuring a virus population. For example, a flow sensor that is sensitive to a toilet flush can be a contamination sensor that detects contamination of a toilet in the enclosed space.

If the sensor (e.g., sensor 290) indicates no occupancy in or no entry into the enclosed space (YES branch at step 234), the controller can (1) modify the UV disinfection assembly to the open state; or (2) maintain the UV disinfection assembly in the open state. If the sensor indicates occupancy in or entry into the enclosed space (NO branch at step 234), the controller can (3) modify the UV disinfection assembly to the closed state; or (4) maintain the UV disinfection assembly in the closed state (step 236). In both cases (both branches of step 234), the controller can activate or continue the disinfection operation.

FIG. 12 is an elevational schematic view of a disinfection system 310, including a housing 312 and a UV disinfection assembly 314 housed in the housing 312, according to an embodiment of the present disclosure. A portion 318 of the disinfection system 310 is shown in greater detail in FIG. 13. The UV disinfection assembly 314 can include an array of UV emitters 256. Twelve of the UV emitters 256 are shown in FIG. 13. The disinfection system 310 can be similar to the disinfection system 250 (FIG. 8) in some respects, including a motor 288, a button 292, a controller 296, a warning indicator 298, a fan 300, a power supply 294, a sensor 290, an air inlet 280, and an air outlet 282. The disinfection system 310 can also include a UV shield assembly 316. The UV shield assembly 316 can include openings 320 and the UV shield assembly 316 can be adjustable (repositionable) between a closed state (FIG. 14) and an open state (FIG. 13). The movement of the UV shield assembly 316 is shown as direction 324 (vertical direction, along longitudinal axis of elongate housing 312) in FIG. 14. When the UV shield assembly 316 is in the open state (FIG. 13), the openings 320 can overlap the UV emitters 256 and the UV electromagnetic radiation emitted from the UV emitters 256 can be transmitted through the disinfection system's front face 326 into the enclosed space. When the UV shield assembly 316 is in the closed state (FIG. 14), the openings 320 can be offset from the UV emitters 256 and the UV electromagnetic radiation can be substantially blocked from being transmitted into the enclosed space. A cross-sectional view of the disinfection system 310, taken along line C-D (FIG. 13), is shown in FIG. 15. The UV emitters 256 can be positioned in the air flow passageway 330 (extending between the air inlet 280 and the air outlet 282) regardless of the open or closed state of the UV shield 316. The UV emitters 256 can thus irradiate the air flowing in the air flow passageway 330.

The disinfection system 310 can be positioned in a corner of an enclosed space (e.g., a room), with the elongate housing 312 extending between a bottom end 270 at the floor of the enclosed space and a top end 272 at the ceiling of the enclosed space. The housing 312 can include a first sidewall 334 and a second sidewall 336 positioned against respective walls of the enclosed space that intersect at the corner. The first sidewall 334 and the second sidewall 336 are joined at a longitudinal corner 338 extending between the opposite ends (270, 272) of the elongate housing 312. The front face 326 can face toward the enclosed space. The UV shield assembly 316 can be adjusted (repositioned) between the closed state and the open state by the motor 288. The UV shield assembly 316 can in some cases be sealable; when the UV shield assembly 316 is in the closed state, the assembly 316 is sealed. The UV shield assembly 316 can in some cases function as a protective cover for the UV emitters 256 when the UV shield assembly 316 is in the closed state and the UV emitters 256 are not in use. The rotatable UV disinfection assembly (FIG. 8) and the movable UV shield assembly (FIG. 12) are examples of UV electromagnetic radiation directors that are adjustable between a closed state and at least one open state.

Figure 16:
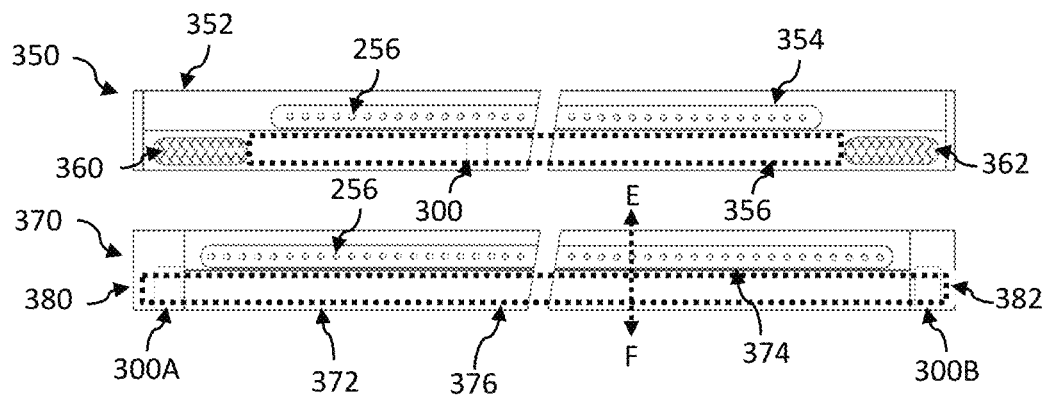
FIGS. 16-18 are schematic views of disinfection systems including an UV disinfection assembly rotatable between an open state and a closed state, according to embodiments of the present disclosure.

FIG. 16 is an elevational schematic view of disinfection systems 350, 370, with each system including a housing (352 and 372 respectively) and a UV disinfection assembly (354 and 374, respectively) housed in the housing (352 and 372, respectively). Each UV disinfection assembly 350, 370 can include UV emitters 256. Disinfection system can 350 can include an air inlet 360 and an air outlet 362, with an air flow passageway 356 extending between the air inlet 360 and the air outlet 362. A fan 300 can be located in the middle of the air flow passageway 376. Disinfection system 370 can include an air inlet 380 and an air outlet 382, with an air flow passageway 376 extending between the air inlet 380 and the air outlet 382. Multiple fans can be located in the air flow passageway 376, for example a first fan 300A near the air inlet 380 and a second fan 300B near the air outlet 382. As shown in FIG. 16, the air inlets/outlets can be oriented in different directions: parallel to the longitudinal axis and facing toward the viewer (e.g., inlet 360 and outlet 362), and perpendicular to the longitudinal axis and facing sideways away from each other (e.g., inlet 380 and outlet 382). Disinfection systems 350, 370 can be installed in or on a wall of an enclosed space or be suspended from a ceiling of an enclosed space.

Figures 17, 18:
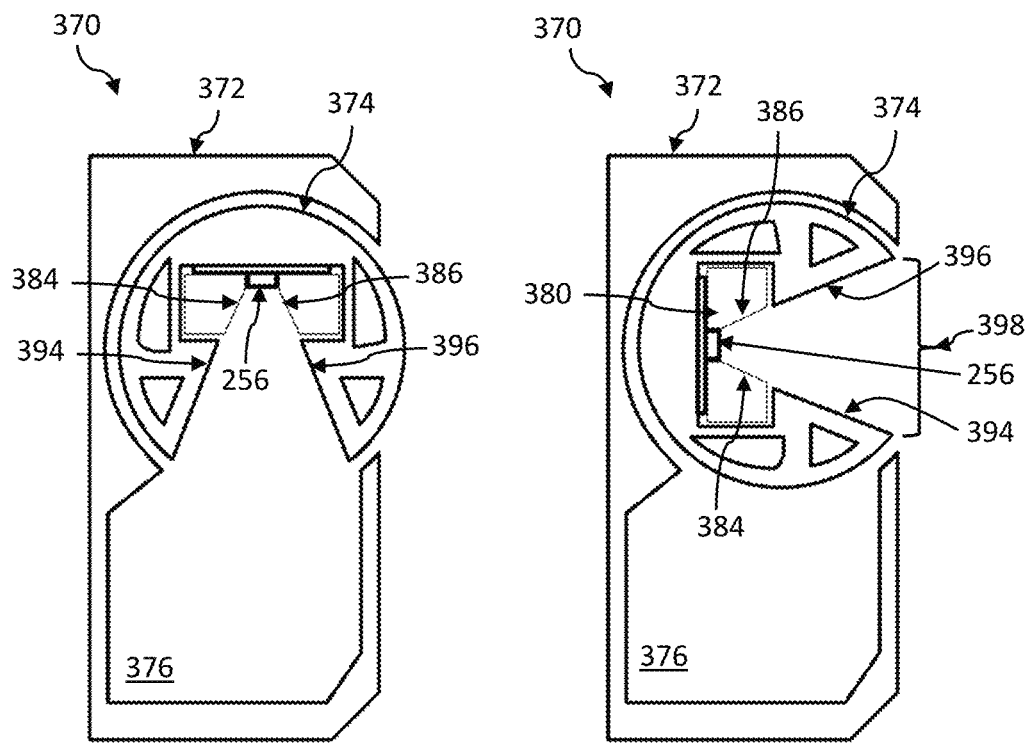

Cross-sectional schematic views of the disinfection system 370, taken along line E-F (FIG. 16), are shown in FIGS. 17 and 18. The UV disinfection assembly 374 can be repositionable (e.g., rotatable) along its longitudinal axis to an open state (shown in FIG. 18) and a closed state (shown in FIG. 17). The rotation of the UV disinfection assembly 374 can be performed by a motor (not shown). Such a motor can be under the control of a controller. FIG. 17 depicts the UV disinfection assembly 374 in a closed state, in which the UV disinfection assembly has been rotated along its longitudinal axis by approximately 90° (clockwise) from the orientation shown in FIG. 18. In the open state, the UV emitters 256 can be oriented such that UV electromagnetic radiation emitted from the UV emitters 256 is directed towards the front opening 398 of the disinfection system 370. The front opening 398 can face towards the enclosed space. UV electromagnetic radiation from the UV emitters 256 can be transmitted into the enclosed space when the UV disinfection assembly 374 is in the open state. When the rotatable UV disinfection assembly 374 is in the closed state (FIG. 17), the UV emitters 256 can be positioned in the air flow passageway 376, and the UV electromagnetic radiation from the UV emitters 256 can be transmitted into the air flow passageway 376. The UV emitters 256 can irradiate the air flowing in the air flow passageway 376. The rotatable UV disinfection assembly 374 (FIGS. 17, 18) can be examples of UV electromagnetic radiation directors.

In the example shown, the UV emitters 256 are located in packages 380 that have reflective sidewalls 384, 386 surrounding the UV emitters 256. The UV disinfection assembly 374 can also have reflective sidewalls 394, 396 that are approximately aligned to the package sidewalls 384, 386. These sidewalls 384, 386, 394, 396 can assist in steering the UV electromagnetic radiation in certain directions.

Figure 19:
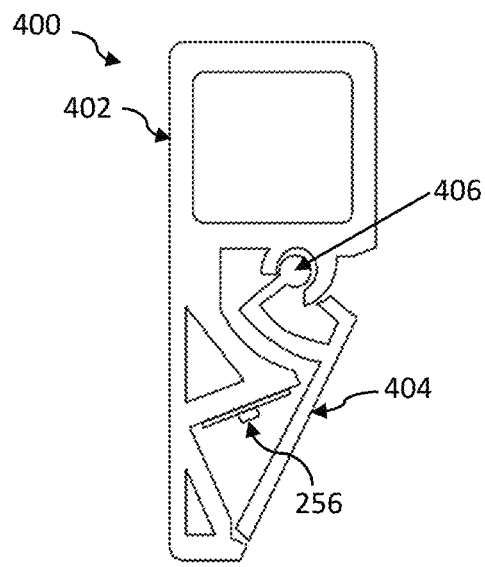
FIGS. 19 and 20 are schematic cross-sectional views of a disinfection system including an UV shield assembly movable between an open state and a closed state, according to embodiments of the present disclosure.
Figure 20:
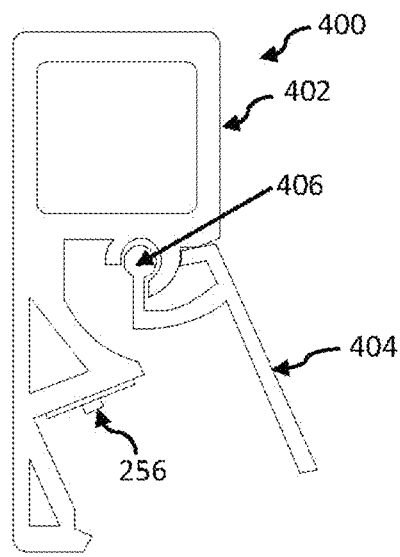

FIGS. 19 and 20 are schematic cross-sectional elevational views of a disinfection system 400 according to an embodiment of the present disclosure. The system 400 can include a housing 402, UV emitters 256, and a rotatable UV shield assembly 404 that is pivotable about a fulcrum 406. FIG. 19 shows the UV shield assembly 404 in a closed state, and FIG. 20 shows the UV shield assembly 404 in an open state. UV electromagnetic radiation from the UV emitters 256 can be transmitted into the enclosed space when the UV shield assembly 404 is in the open state (FIG. 20). Transmission of UV electromagnetic radiation into the enclosed space can be substantially blocked when the UV shield assembly 404 is in the closed state (FIG. 19). The pivoting of the UV shield assembly 404 can be done by a motor (not shown) under control of a controller. The repositionable (e.g., pivotable) UV shield assembly 404 (FIGS. 19, 20) can be an example of an UV electromagnetic radiation director.

Figure 21:
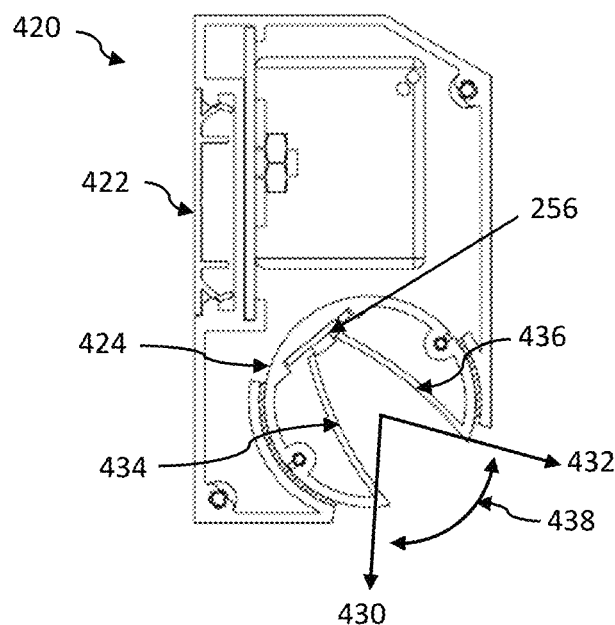
FIG. 21 is a schematic cross-sectional view of a disinfection system including an UV disinfection assembly rotatable to multiple open positions, according to an embodiment of the present disclosure.

FIG. 21 is a schematic cross-sectional elevational view of a disinfection system 420 according to an embodiment of the present disclosure. They system 420 can include a housing 422, UV emitters 256, and a rotatable UV disinfection assembly 424 that is rotatable around its longitudinal axis (range of rotation for the assembly 424 schematically shown by arc 438). The UV disinfection assembly 424 can include concave curved reflectors 434, 436 that surround the UV emitters 256. The concave curved reflectors 434, 436 can be focusing optics that focus the UV electromagnetic radiation. The UV disinfection assembly 424 can be repositionable to multiple open states, with each open state corresponding to a respective angular orientation of the UV electromagnetic radiation in the enclosed space. For example, a first open state can include UV electromagnetic radiation that is transmitted predominantly directed towards a first direction 430, and a second open state in which the UV electromagnetic radiation is predominantly directed towards a second direction 432 rotated from the first direction. Disinfection system 420 can be an example of a system in which the aim or direction of the UV electromagnetic radiation can be changed. The rotation of the UV disinfection assembly 424 can be performed by a motor (not shown) under control of a controller. The rotatable UV disinfection assembly 424 can be an example of a UV electromagnetic radiation director.

Figure 22:
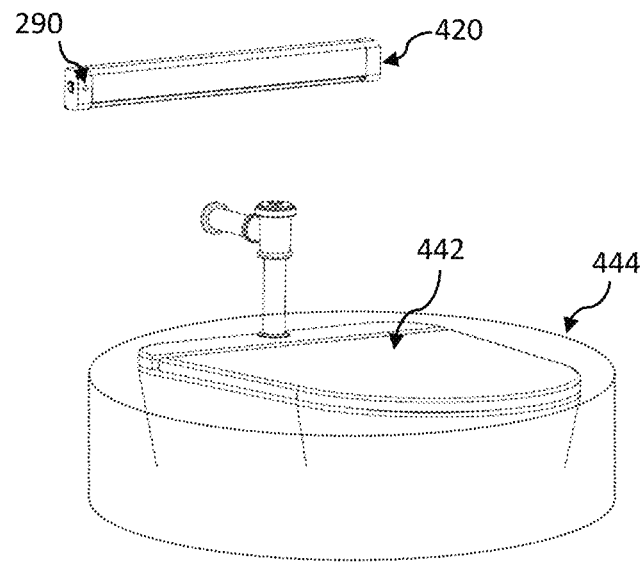
FIG. 22 is a perspective view of a disinfection system configured for use in a toilet, according to an embodiment of the present disclosure.
Figure 23:
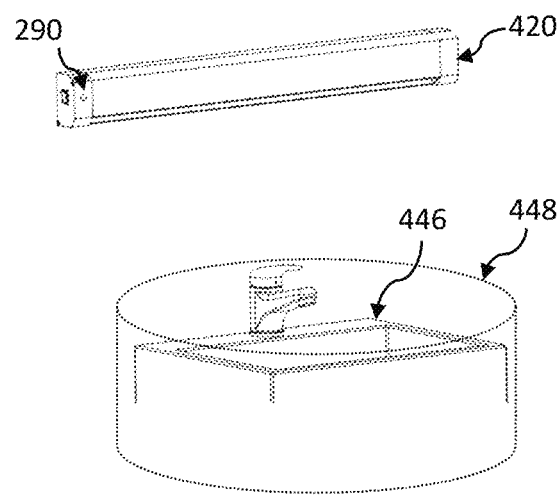
FIG. 23 is a perspective view of a disinfection system configured for use in a sink, according to an embodiment of the present disclosure.

Use cases in which the aiming capability is useful are shown in FIGS. 22 and 23. FIG. 22 shows a toilet disinfection system and FIG. 23 shows a sink disinfection system, according to embodiments of the present disclosure. In FIG. 22, a target zone 444 can include a toilet bowl 442, and in FIG. 23 a target zone 448 can include a sink basin 446. In the examples shown, the disinfection systems are shown as being installed on or in the wall above the target zones. In both cases, the target zone can be quite small compared to a surrounding enclosed space (e.g., the bathroom or kitchen) and it is desirable to achieve a predetermined UV dose (e.g., 3.0 mJ/cm2 or greater) at the target zone 444, 448. It may be less desirable to achieve the predetermined dose elsewhere in the enclosed space outside of the target zone 444, 448. Accordingly, the rotatable UV disinfection assembly 420 can be adjusted (rotated) to one of multiple open states to adjust the aim of the UV electromagnetic radiation, and focusing optics (e.g., focusing optics 434, 436 described in FIG. 21) can focus the UV electromagnetic radiation, such that the UV electromagnetic radiation irradiates target zone 444, 448 that is quite small compared to the enclosed space.

Figures 24, 25:
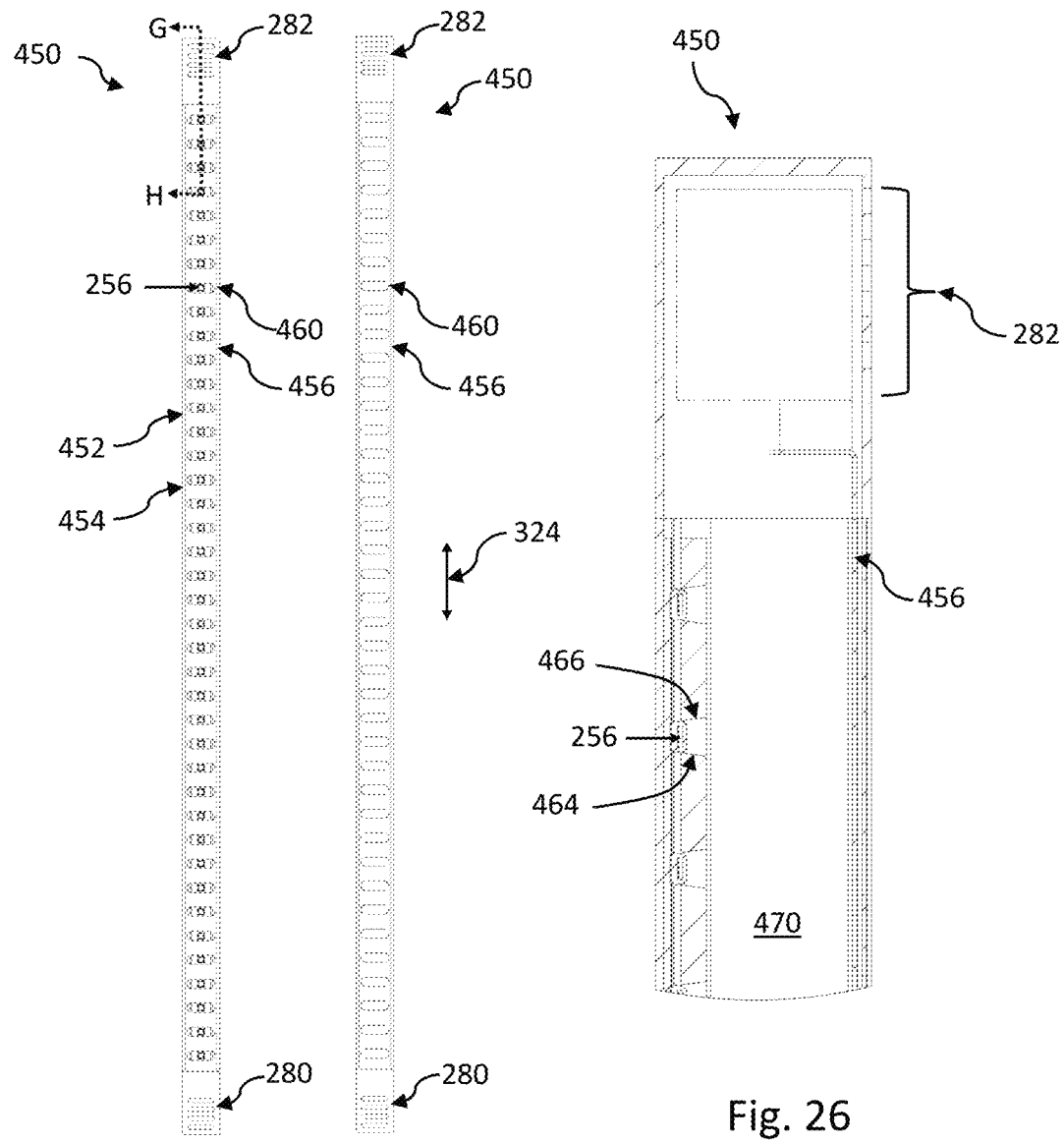

FIGS. 24 and 25 are elevational schematic views of a disinfection system 450 according to embodiments of the present disclosure. The system 450 can include a housing 452 and a UV disinfection assembly 454 housed in the housing 452. The UV disinfection assembly 454 can include an array of UV emitters 256. The disinfection system 450 can also include a UV shield assembly 456. The UV shield assembly 456 can include openings 460, and the UV shield assembly 456 can be repositionable (e.g., adjustable) between an open state (FIG. 24) and a closed state (FIG. 25). The movement of the UV shield assembly 456 is shown as direction 324 (vertical direction, along longitudinal axis of elongate housing 452) in FIG. 25. The movement (e.g., sliding) of the UV shield assembly 456 can be performed by a motor (not shown) under control of a controller. When the UV shield assembly 456 is in the open state (FIG. 24), the openings 460 can overlap the UV emitters 256 and the UV electromagnetic radiation emitted from the emitter 256 can be transmitted into the enclosed space. When the UV shield assembly 456 is in the closed state (FIG. 25), its openings 460 can be offset from the UV emitters 256 and the UV electromagnetic radiation can be substantially blocked from being transmitted into the enclosed space. A cross-sectional schematic view of the disinfection system 450, taken along line G-H (FIG. 24), is shown in FIG. 26. The UV emitters 256 can be positioned in the air flow passageway 470 (extending between the air inlet 280 and the air outlet 282) regardless of the open or closed state of the UV shield assembly 456. The array of UV emitters 256 can extend through most of the length of the air flow passageway 470 between the air inlet 280 and the air outlet 282. The direction of air flow in the air flow passageway 470 can be approximately parallel to the direction of movement of the UV shield assembly 456, along direction 324. Disinfection system 450 can be an example of a linear disinfection fixture.

Figure 27:
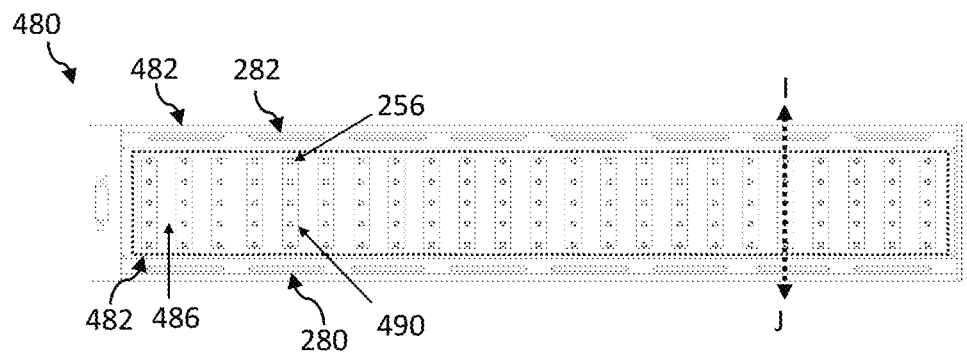
Figure 28:
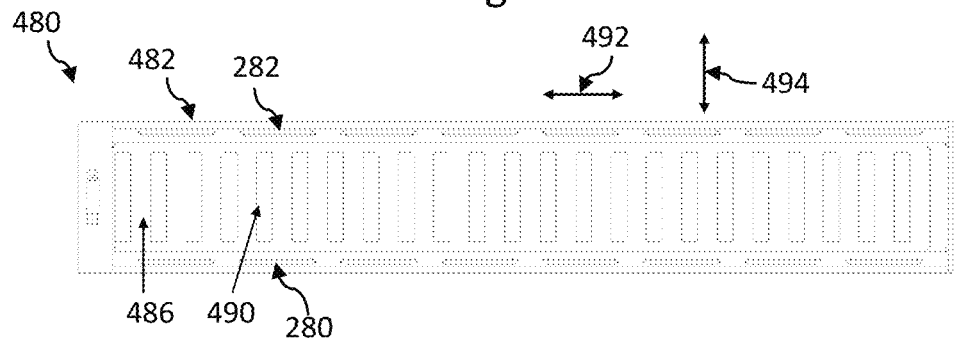
Figure 29:
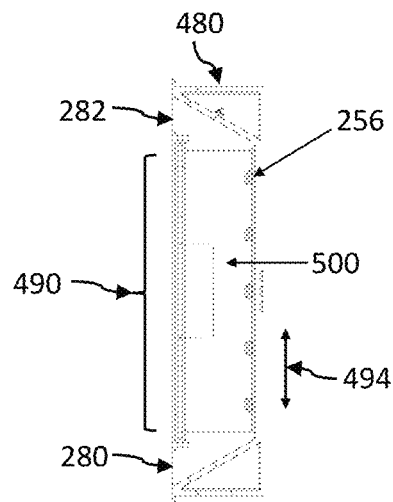

FIGS. 27 and 28 are schematic elevational views of a disinfection system 480. The system 480 can include a housing 482 and a UV disinfection assembly 484 housed in the housing 482. The UV disinfection assembly 484 can include UV emitters 256 arranged in a planar array. The disinfection system 480 can include a UV shield assembly 486. The UV shield assembly 486 can include openings 490, and the UV shield assembly 486 can be repositionable (e.g., adjustable) between an open state (FIG. 27) and a closed state (FIG. 28). The movement of the UV shield assembly 486 is shown as direction 492 (horizontal direction) in FIG. 28. The movement (e.g., sliding) of the UV shield assembly 486 can be performed by a motor (not shown) under control of a controller. When the UV shield assembly 486 is in the open state (FIG. 24), the openings 490 can overlap the UV emitters 256 and the UV electromagnetic radiation emitted from the emitters 256 can be transmitted into the enclosed space. When the UV shield assembly 486 is in the closed state (FIG. 25), the openings 460 are offset from the UV emitters 256 and the UV electromagnetic radiation can be substantially blocked from being transmitted into the enclosed space. A cross-sectional view of the disinfection system 480, taken along line I-J (FIG. 27), is shown in FIG. 29. The UV emitters 256 can be positioned in the air flow passageway 500 (extending between the air inlet 280 and the air outlet 282) regardless of the open or closed state of the UV shield 486. The direction of air flow in the air flow passageway 500 is shown as direction 494 (vertical direction) in FIGS. 28, 29 and can be approximately perpendicular to the direction of movement of the UV shield assembly 486, along direction 492. Disinfection system 480 can be an example of a planar disinfection fixture.

Figure 30:
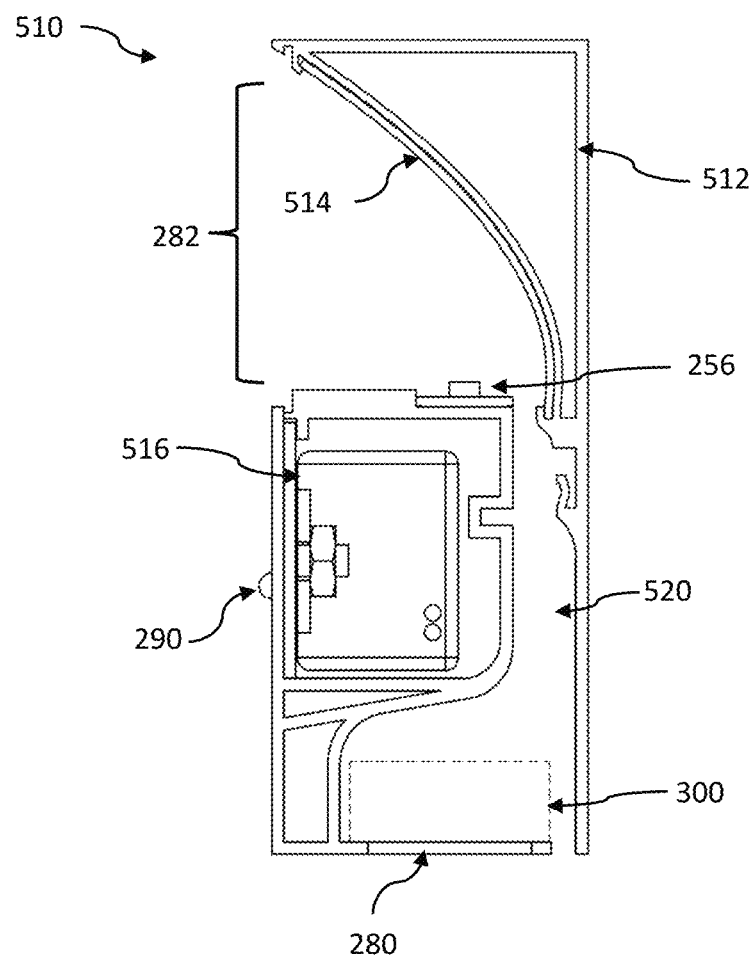
FIGS. 30 and 31 are schematic cross-sectional views of disinfection systems in which the UV emitters are positioned in air flow passageways, according to embodiments of the present disclosure.

FIG. 30 is a schematic cut-away elevational view of a disinfection system 510 according to an embodiment of the present disclosure. The system 510 can include a housing 512, UV emitters 256, a sensor 290 facing outwards (towards the direction where the enclosed space would be located), and an electronics portion 516. The housing can include an air inlet 280, an air outlet 282, and an air flow passageway 520 extending between the air inlet 280 and the air outlet 282. In the example shown, a fan 300 can be located in the air flow passageway 520 near the air inlet 280. The UV emitters 256 can be positioned in the air flow passageway 520 and the UV emitters 256 can irradiate the air flowing in the air flow passageway 520. The electronics portion 516 can include a controller, a power supply, and UV emitter driver circuitry. The controller is in communication with the sensor 290 and the UV emitters 256 and can be configured to control operation of the UV emitters 256 to carry out disinfection operations.

The housing 512 can include a concave curved reflector 514, positioned in the air flow passageway 520 near the air flow outlet 282. The reflector 514 can be configured to reflect the UV electromagnetic radiation from the UV emitters 256 towards the air outlet 282 into the enclosed space. The reflector 514 and the UV emitters 256 can be positioned such that air flowing in the air flow passageway 520 passes between the emitters 256 and the reflector 514. In some cases, the UV emitters 256 can be arranged in an array. In some cases, the disinfection system 510 can be a linear fixture, the reflector 514 can be a linear reflector, and the array of UV emitters 256 can be a linear array. A longitudinal axis of the linear array can be approximately parallel to a longitudinal axis of the linear reflector. The linear reflector can curved; the linear reflector can focus the electromagnetic radiation of the emitters 256 to a beam having a beam angle of 40 degrees or less, or 20 degrees or less.

The disinfection system 510 can be configured such that a disinfection operation is suspended or deactivated when the sensor 290 indicates occupancy in or entry into the enclosed space. Alternatively, the disinfection system 510 can be a system for disinfecting a room in which the housing 512 is positioned such that the UV electromagnetic radiation is directed above a human's line-of-sight in the room. By positioning the housing 512 in this way, it becomes possible to carry out disinfection operations when there is occupancy in or entry into the room. Accordingly, the disinfection system 510 can be configured to be "always-on." In such an implementation, it may be possible to omit the sensor 290 and the controller.

Figure 31:
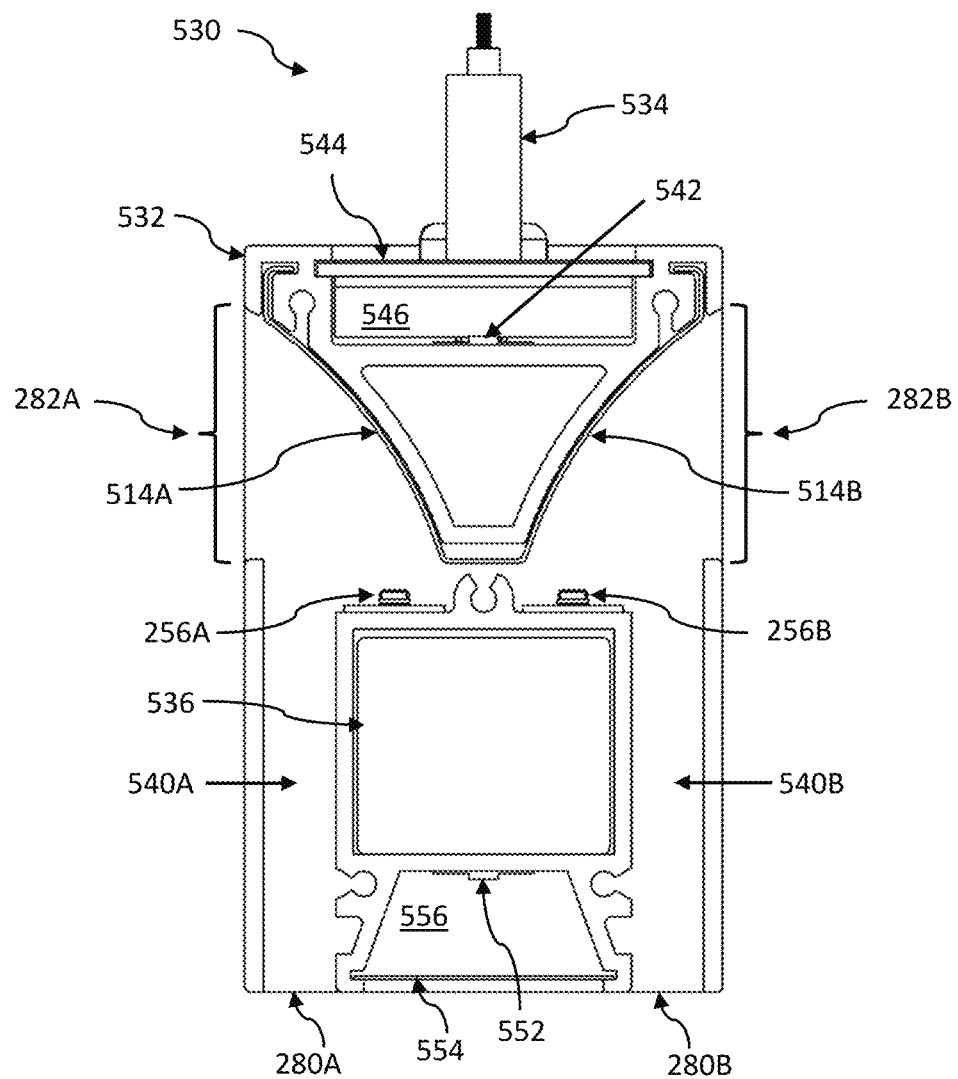

FIG. 31 is a schematic cut-away elevational view of a disinfection system 530 according to an embodiment of the present disclosure. The system 530 can include a housing 532, UV emitters 256A, 256B (hereinbelow, the A and B designations refer to components on the left and right sides respectively in the example shown in FIG. 31), and an electronics portion 536. The housing can include air inlets 280A, 280B, air outlets 282A, 282B, and air flow passageways 540A, 540B extending between the respective air inlets 280A, 280B and air outlets 282A, 282B, respectively.

The UV emitters 256A, 256B can be positioned in the respective air flow passageways 540A, 540B and the UV emitters 256A, 256B can irradiate the air flowing in the respective air flow passageways 540A, 540B. The electronics portion 536 can include a power supply, UV emitter driver circuitry, and visible light emitter driver circuitry. The electronics portion 536 can also include a controller, configured to control operation of the UV emitters 256A, 256B to carry out disinfection operations.

The housing 532 can include concave curved reflectors 514A, 514B, positioned in the respective air flow passageways 540A, 540B near the respective air flow outlets 282A, 282B. The reflectors 514A, 514B can be configured to reflect the UV electromagnetic radiation from the UV emitters 256A, 256B towards the respective air outlets 282A, 282B into the enclosed space. In the example shown, the UV electromagnetic radiation can be directed both rightward and leftward into the enclosed space from the disinfection system 530. The reflectors 514A, 514B and the respective UV emitters 256A, 256B can be positioned such that air flowing in the respective air flow passageways 540A, 540B passes between the reflectors 514A, 514B and the UV emitters 256A, 256B. In some cases, each set of UV emitters 256A, 256B can be arranged in an array. In some cases, disinfection system 530 can be a linear fixture, and each of the reflectors 514A, 514B can be a linear reflector, and each array of UV emitters can be a linear array. A longitudinal axis of each linear array can be approximately parallel to a longitudinal axis of the corresponding linear reflector. In some cases, each linear reflector can be curved; each linear reflector can focus the electromagnetic radiation to a beam having a beam angle of 40 degrees or less, or 20 degrees or less.

In the example shown, disinfection system 530 can also include suspension hardware 534 for suspending the housing 532 from the ceiling of the enclosed space. Accordingly, the disinfection system 530 can be a system for disinfecting a room in which the housing 532 is positioned such that the UV electromagnetic radiation is directed above a human's line-of-sight in the room. In some cases, the disinfection system 530 can be configured to be "always-on." The suspension hardware 534 can also include power supply cabling connected to a power supply. The disinfection system 530 can be implemented as a hanging linear pendant fixture or a hanging circular pendant fixture. The disinfection system 530 can also include visible light emitters 542 and 552. In some cases, the visible light emitters can be visible light LEDs. The visible light emitter driver circuitry (located in the electronics portion 536) can drive the visible light emitters. The visible light emitters 552 can be positioned in a cavity 556 and are configured to emit visible light downward. The visible light emitted by the visible light emitters 552 can be diffused an optional diffuser 554 before entering the enclosed space. The visible light emitters 542 can be positioned in a cavity 546 and can be configured to emit visible light upward. The visible light emitted by the visible light emitters 542 can be diffused by a diffuser 544 before entering the enclosed space.

The visible light emitters 542, 552 can improve the functionality of the disinfection system 530. The visible light emitters 542, 552 and the UV emitters 256A, 256B can be operated asynchronously. The visible light emitters 542, 552 can be illuminate the enclosed space with white light or visible light illumination. The system 530 can include a lifetime counter to track a cumulative UV dose emitted by the UV emitters 256A, 256B and the light emitters 542, 552 can be implemented as a warning indicator, configured to indicate when the cumulative UV dose exceeds a predetermined cumulative UV dose. For example, light emitters 542, 552 can include a non-white light emitter (such as red LEDs). The visible light emitters 542, 552 can be visible from the enclosed space. The visible light emitters 542, 552 can be implemented as a non-white visible indicator light, configured to indicate when the disinfection operation is active.

FIGS. 32, 33, and 34 are schematic cross-sectional elevational views of a disinfection system 560, according to embodiments of the present disclosure. The system 560 can include a housing 562, a rotatable UV disinfection assembly 564 that is repositionable (pivotable) about a fulcrum 566, and an electronics portion 568. The rotatable UV disinfection assembly 564 can include UV emitters 256 and concave curved reflector 514. The concave curved reflector 514 can be configured to reflect the UV electromagnetic radiation emitted from the UV emitters 256 into the enclosed space. In some cases, the UV emitters 256 can be arranged in an array. The electronics portion 568 can include a controller, a power supply, and UV emitter driver circuitry. The controller is in communication with the UV emitters 256 and the UV disinfection assembly 564, and can be configured to control operation of the UV emitters 256 and the UV disinfection assembly 564 to carry out disinfection operations. The rotatable UV disinfection assembly 564 (FIGS. 32, 33, and 34) can be an example of UV electromagnetic radiation directors.

In some cases, the disinfection system 560 can be a linear fixture, the reflectors 514 can be a linear reflector, and the array of UV emitters can be a linear array. A longitudinal axis of the linear array can be approximately parallel to a longitudinal axis of the linear reflector. The linear reflector can be concave curved. In some cases, the reflector 514 can focus the electromagnetic radiation to a beam having a beam angle of 40 degrees or less, or 20 degrees or less. Alternatively, the UV disinfection assembly 564 can include a lens configured to focus the electromagnetic radiation to a beam having a beam angle of 40 degrees or less. Illustrative UV rays 568 after reflection by the reflector 514 are shown in FIG. 32.

FIGS. 32, 33, and 34 illustrate respective orientation states of the UV disinfection assembly 564. Each orientation state can correspond to a respective angular orientation of the UV electromagnetic radiation into the enclosed space. FIG. 32 shows the UV disinfection assembly 564 in a "collapsed" state. This corresponds to the UV rays propagating in approximately the 9 o'clock direction. FIG. 33 shows the UV disinfection assembly 564 rotated counterclockwise by approximately 60 degrees from the orientation state shown in FIG. 32. This corresponds to the UV rays propagating in approximately the 7 o'clock direction. FIG. 34 shows the UV disinfection assembly 564 rotated counterclockwise by approximately 90 degrees from the orientation state shown in FIG. 32. This corresponds to the UV rays propagating in approximately the 6 o'clock direction. The rotation (pivoting) of the UV disinfection assembly 564 can be performed by a motor (not shown) under control of the controller. The UV disinfection assembly 564 can be configured to cycle through these orientation states shown in FIGS. 33 and 34 in a "sweeping" motion.

For example, consider a use case in which the enclosed space is a room and the system 560 (housing 562) is positioned in a corner of the room, on or in a ceiling of the room, or on or in a wall of the room, or suspended from the ceiling of the room. System 560 can be positioned such that the UV disinfection assembly 564, in the orientation states shown in FIGS. 33 and 34, directs the UV electromagnetic radiation towards a first target zone located below system 560. The first target zone can be at or below a human's line-of-sight. For example, the first target zone can include the floor, sinks, toilets, beds, desks, chairs, and tables. Additionally, in the orientation state shown in FIG. 32, the UV disinfection assembly can direct the UV electromagnetic radiation towards a second target zone that is laterally displaced from the system 560. The second target zone can be above a human's line-of-sight. The UV electromagnetic radiation can be directed to the second target zone when people are present in the room. The UV electromagnetic radiation can be directed to the first target zone when people are not present in the room. In some cases, the disinfection system 560 can be configured to be "always-on." If the UV disinfection assembly 564 is configured to cycle through the orientation states shown in FIGS. 33 and 34, the disinfection system 560 "sweeps" the first target zone.

Figure 35:
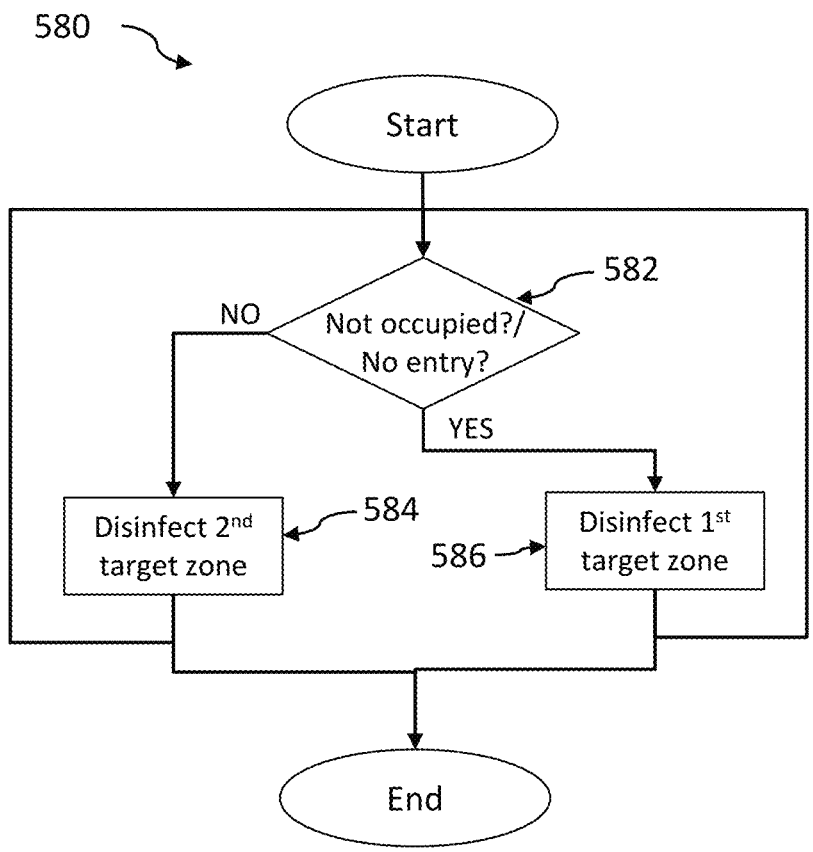
FIG. 35 is a flow diagram of a method of disinfecting an enclosed space, according to an embodiment of the present disclosure.

A flow diagram of a method 580 of disinfecting an enclosed space is shown in FIG. 35, according to an embodiment of the present disclosure. The method 580 can be implemented using the disinfection system 560 as described with reference to FIGS. 32-34. The method 580 can include steps 582, 584, and 586. The UV disinfection assembly can be rotated to orientations states, such as orientation states shown in FIGS. 33 and 34, and can direct the UV electromagnetic radiation towards a first target zone (step 586) when there is an indication or determination of no occupancy in or no entry into the enclosed space (YES branch at step 582). The UV disinfection assembly can be rotated to an orientation state, such as the orientation state shown in FIG. 32, and can direct the UV electromagnetic radiation towards a second target zone (step 584) when there is an indication or determination of occupancy in or entry into the enclosed space (NO branch at step 582).

In some use cases, the controller can be in communication with a sensor to detect occupancy in or entry into the enclosed space. For example, there is indication or determination of no occupancy in or no entry into the enclosed space when the sensor indicates no occupancy in or no entry into the enclosed space (YES branch at step 582). For example, there is an indication or determination of occupancy in or entry into the enclosed space when the sensor indicates occupancy in or entry into the enclosed space (NO branch at step 582).

In some use cases, an indication or determination can be obtained by determining whether the current time is within a predetermined time period. For example, there is indication or determination of no occupancy in or no entry into the enclosed space when a current time is within a predetermined time period (YES branch at step 582). For example, there is indication or determination of occupancy in or entry into the enclosed space when the current time is outside the predetermined time period (NO branch at step 582). The predetermined time period can be a time period when people would not be present in the enclosed space.

What is claimed is:

1. A system for disinfecting an enclosed space, comprising:
    a housing comprising an air inlet, an air outlet, and an air flow passageway extending between the air inlet and the air outlet;
    ultraviolet (UV) emitters for selectively emitting UV electromagnetic radiation;
    a sensor to detect occupancy in or entry into an enclosed space;
    a UV electromagnetic radiation director; and
    a controller in communication with the UV emitters and the sensor and configured to control operation of the UV emitters to carry out disinfection operations, each of a predetermined UV dose;
    wherein the UV electromagnetic radiation director is adjustable between a closed state and at least one open state, transmission of UV electromagnetic radiation into the enclosed space being substantially blocked when the UV electromagnetic radiation director is in the closed state, UV electromagnetic radiation being transmitted into the enclosed space when the UV electromagnetic radiation director is in the at least one open state;
    the UV emitters are positioned in the air flow passageway in at least one of the states of the UV electromagnetic radiation director including the closed state;
    if the UV electromagnetic radiation director is in the closed state, the controller activates the disinfection operation when first activation conditions are satisfied;
    if the UV electromagnetic radiation director is in the at least one open state, the controller activates the disinfection operation when second activation conditions are satisfied;
    the second activation conditions comprise: (2A) the sensor indicating no occupancy in or no entry into the enclosed space;
    the controller suspends or deactivates the disinfection operation when the UV electromagnetic radiation director is in the at least one open state and the sensor indicates occupancy in or entry into the enclosed space; and
    the disinfection operation comprises selectively emitting, by the UV emitters, UV electromagnetic radiation,
    wherein the UV electromagnetic radiation director comprises a UV disinfection module comprising the UV emitters, rotatable along its longitudinal axis between the closed state and the at least one open state.

2. The system of claim 1, wherein the first activation conditions comprise: (1A) passage of a time period greater than a minimum inter-operation time (MIOT) since completion of a previous one of the disinfection operations.

3. The system of claim 1, wherein the second activation conditions comprise: (2B) passage of a time period greater than a minimum inter-operation time (MIOT) since completion of a previous one of the disinfection operations.

4. The system of claim 1, additionally comprising a lifetime counter to track a cumulative UV dose emitted by the UV emitters.

5. The system of claim 4, additionally comprising a warning indicator, configured to indicate when the cumulative UV dose exceeds a predetermined cumulative UV dose.

6. The system of claim 1, additionally comprising focusing optics to focus the UV electromagnetic radiation, such that the UV electromagnetic radiation irradiates a target zone that is smaller than the enclosed space when the disinfection operation is active and the UV electromagnetic radiation director is in the at least one open state.

7. The system of claim 6, the target zone includes a toilet.

8. The system of claim 6, the target zone includes a sink.

9. The system of claim 1, wherein the enclosed space is a room and the housing is positioned in a corner of the room, on or in a ceiling of the room, or on or in a wall of the room, or suspended from the ceiling of the room.

10. The system of claim 1, wherein the UV disinfection module is rotatable to a plurality of open states, each open state corresponding to a respective angular orientation of the UV electromagnetic radiation in the enclosed space.

11. The system of claim 1, wherein the UV electromagnetic radiation director comprises a UV shield assembly, movable between the closed state and the at least one open state.

12. The system of claim 11, wherein the UV shield assembly is sealed when in the closed state.

13. The system of claim 11, wherein the UV shield assembly functions as a protective cover for the UV emitters when the UV shield assembly is in the closed state and the UV emitters are not in use.

14. The system of claim 1, the sensor is a door-open sensor at a door of the enclosed space.

15. The system of claim 1, wherein the UV electromagnetic radiation is in a range of 200 nm to 300 nm.

16. The system of claim 1, wherein the predetermined UV dose is 3.0 mJ/cm$^2$ or greater, measured at a target zone in the enclosed space.

17. The system of claim 1, wherein UV emitters are selected from: light-emitting diodes (LEDs), laser diodes, and lamps.

18. The system of claim 1, additionally comprising an air mover configured to move air through the air flow passageway.

19. The system of claim 1, additionally comprising a communication module for communication with an external device.

20. The system of claim 1, additionally comprising a visible light emitter that is visible from the enclosed space.

21. The system of claim 20, wherein the visible light emitter and the UV emitters are operated asynchronously.

22. The system of claim 20, wherein the visible light emitter is a non-white visible indicator light, configured to indicate when the disinfection operation is active.

23. A system for disinfecting an enclosed space, comprising:
- a housing comprising an air inlet, an air outlet, and an air flow passageway extending between the air inlet and the air outlet;
- ultraviolet (UV) emitters for selectively emitting UV electromagnetic radiation;
- a sensor to detect occupancy in or entry into an enclosed space; and
- a UV electromagnetic radiation director; and
- a controller in communication with the UV emitters and the sensor and configured to control operation of the UV emitters to carry out disinfection operations, each of a predetermined UV dose;
- wherein the UV electromagnetic radiation director is adjustable between a closed state and at least one open state, transmission of UV electromagnetic radiation into the enclosed space being substantially blocked when the UV electromagnetic radiation director is in the closed state, UV electromagnetic radiation being transmitted into the enclosed space when the UV electromagnetic radiation director is in the at least one open state;
- the UV emitters are positioned in the air flow passageway in at least one of the states of the UV electromagnetic radiation director including the closed state;
- the controller is in communication with the UV electromagnetic radiation director and is configured to control operation of the UV electromagnetic radiation director;
- if the sensor indicates no occupancy in or no entry into the enclosed space, the controller activates or continues the disinfection operation and (1) changes the UV electromagnetic radiation director to the at least one open state or (2) maintains the UV electromagnetic radiation director in the at least one open state when activation condition(s) are satisfied;
- if the sensor indicates occupancy in or entry into the enclosed space, the controller activates or continues the disinfection operation and (3) changes the UV electromagnetic radiation director to the closed state or (4) maintains the UV electromagnetic radiation director to the closed state when activation condition(s) are satisfied; and
- the disinfection operation comprises selectively emitting, by the UV emitters, UV electromagnetic radiation,
- wherein the UV electromagnetic radiation director comprises a UV disinfection module comprising the UV emitters, rotatable along its longitudinal axis between the closed state and the at least one open state.

24. The system of claim 23, wherein the activation condition(s) comprise: (A) passage of a time period greater than a minimum inter-operation time (MIOT) since completion of a previous one of the disinfection operations.

25. The system of claim 23, wherein the activation condition(s) comprise: (B) a qualified human input through a human-machine interface (HMI) in communication with the controller.

26. The system of claim 23, wherein the activation condition(s) comprise: (C) an indication of contamination in the enclosed space from a contamination sensor in communication with the controller.

27. The system of claim 23, additionally comprising a lifetime counter to track a cumulative UV dose emitted by the UV emitters.

28. The system of claim 27, additionally comprising a warning indicator, configured to indicate when the cumulative UV dose exceeds a predetermined cumulative UV dose.

29. The system of claim 23, additionally comprising focusing optics to focus the UV electromagnetic radiation, such that the UV electromagnetic radiation irradiates a target zone that is smaller than the enclosed space when the disinfection operation is active and the UV electromagnetic radiation director is in the at least one open state.

30. The system of claim 29, the target zone includes a toilet.

31. The system of claim 29, the target zone includes a sink.

32. The system of claim 23, wherein the enclosed space is a room and the housing is positioned in a corner of the room, on or in a ceiling of the room, or on or in a wall of the room, or suspended from the ceiling of the room.

33. The system of claim 23, wherein the UV disinfection module is rotatable to a plurality of open states, each open state corresponding to a respective angular orientation of the UV electromagnetic radiation in the enclosed space.

34. The system of claim 23, wherein the UV electromagnetic radiation director comprises a UV shield assembly, movable between the closed state and the at least one open state.

35. The system of claim 34, wherein the UV shield assembly is sealed when in the closed state.

36. The system of claim 34, wherein the UV shield assembly functions as a protective cover for the UV emitters when the UV shield assembly is in the closed state and the UV emitters are not in use.

37. The system of claim 23, the sensor is a door-open sensor at a door of the enclosed space.

38. The system of claim 23, wherein the UV electromagnetic radiation is in a range of 200 nm to 300 nm.

39. The system of claim 23, wherein the predetermined UV dose is 3.0 mJ/cm² or greater, measured at a target zone in the enclosed space.

40. The system of claim 23, wherein UV emitters are selected from: light-emitting diodes (LEDs), laser diodes, and lamps.

41. The system of claim 23, additionally comprising an air mover configured to move air through the air flow passageway.

42. The system of claim 23, additionally comprising a communication module for communication with an external device.

43. The system of claim 23, additionally comprising a visible light emitter that is visible from the enclosed space.

44. The system of claim 43, wherein the visible light emitter and the UV emitters are operated asynchronously.

45. The system of claim 43, wherein the visible light emitter is a non-white visible indicator light, configured to indicate when the disinfection operation is active.

46. A system for disinfecting an enclosed space, comprising:
a housing comprising an air inlet, an air outlet, and an air flow passageway extending between the air inlet and the air outlet;
ultraviolet (UV) emitters for selectively emitting UV electromagnetic radiation, the UV emitters being positioned in the air flow passageway, the UV emitters irradiating air flowing in the air flow passageway; and
a controller in communication with the UV emitters and configured to control operation of the UV emitters to carry out disinfection operations;
wherein the disinfection operation comprises selectively emitting, by the UV emitters, UV electromagnetic radiation, at least some of the UV electromagnetic radiation being transmitted into the enclosed space,
wherein the UV electromagnetic radiation director comprises a UV disinfection module comprising the UV emitters, rotatable along its longitudinal axis between the closed state and the at least one open state.

47. The system of claim 46, additionally comprising a lifetime counter to track a cumulative UV dose emitted by the UV emitters.

48. The system of claim 47, additionally comprising a warning indicator, configured to indicate when the cumulative UV dose exceeds a predetermined cumulative UV dose.

49. The system of claim 46, additionally comprising focusing optics to focus the UV electromagnetic radiation, such that the UV electromagnetic radiation irradiates a target zone that is smaller than the enclosed space when the disinfection operation is active.

50. The system of claim 46, wherein the enclosed space is a room and the housing is positioned in a corner of the room or on or in a wall of the room.

51. The system of claim 46, wherein the housing is positioned such that the UV electromagnetic radiation directed above a human's line-of-sight.

52. The system of claim 46, wherein the UV electromagnetic radiation is in a range of 200 nm to 300 nm.

53. The system of claim 46, wherein each disinfection operation is of a predetermined UV dose, the predetermined UV dose being 3.0 mJ/cm² or greater, measured at a target zone in the enclosed space.

54. The system of claim 46, wherein UV emitters are selected from: light-emitting diodes (LEDs), laser diodes, and lamps.

55. The system of claim 46, additionally comprising an air mover configured to move air through the air flow passageway.

56. The system of claim 46, additionally comprising a visible light emitter that is visible from the enclosed space.

57. The system of claim 56, wherein the visible light emitter and the UV emitters are operated asynchronously.

58. The system of claim 56, wherein the visible light emitter is a non-white visible indicator light, configured to indicate when the disinfection operation is active.

59. A system for disinfecting an enclosed space, comprising:
a housing comprising an air inlet, an air outlet, and an air flow passageway extending between the air inlet and the air outlet;
ultraviolet (UV) emitters for selectively emitting UV electromagnetic radiation, the UV emitters being arranged in an array, the UV emitters being positioned in the air flow passageway, the UV emitters irradiating air flowing in the air flow passageway; and
a linear reflector, positioned in the air flow passageway and configured to reflect the UV electromagnetic radiation towards the air outlet into the enclosed space;
wherein the linear reflector and UV emitters are positioned such that air flowing in the air flow passageway passes between them,
wherein the UV electromagnetic radiation director comprises a UV disinfection module comprising the UV emitters, rotatable along its longitudinal axis between the closed state and the at least one open state.

60. The system of claim 59, wherein the array is a linear array and a longitudinal axis of the linear array is approximately parallel to a longitudinal axis of the linear reflector.

61. The system of claim 59, additionally comprising a lifetime counter to track a cumulative UV dose emitted by the UV emitters.

62. The system of claim 59, additionally comprising a warning indicator, configured to indicate when the cumulative UV dose exceeds a predetermined cumulative UV dose.

63. The system of claim 59, wherein the linear reflector is configured to focus the electromagnetic radiation to a beam having a beam angle of 40 degrees or less.

64. The system of claim 59, wherein the enclosed space is a room and the housing is positioned in a corner of the room or on or in a wall of the room.

65. The system of claim 59, wherein the housing is positioned such that the UV electromagnetic radiation is directed above a human's line-of-sight.

66. The system of claim 59, wherein the UV electromagnetic radiation is in a range of 200 nm to 300 nm.

67. The system of claim 59, wherein UV emitters are selected from: light-emitting diodes (LEDs), laser diodes, and lamps.

68. The system of claim 59, additionally comprising an air mover configured to move air through the air flow passageway.

* * * * *